US008817115B1

(12) United States Patent
Venkatachalam

(10) Patent No.: US 8,817,115 B1
(45) Date of Patent: Aug. 26, 2014

(54) SPATIAL ALIGNMENT OF IMAGE DATA FROM A MULTICHANNEL DETECTOR USING A REFERENCE IMAGE

(75) Inventor: Vidya Venkatachalam, Bellevue, WA (US)

(73) Assignee: Amnis Corporation, Seattle, WA (US)

( * ) Notice: Subject to any disclaimer, the term of this patent is extended or adjusted under 35 U.S.C. 154(b) by 713 days.

(21) Appl. No.: 13/102,003

(22) Filed: May 5, 2011

Related U.S. Application Data

(60) Provisional application No. 61/331,760, filed on May 5, 2010.

(51) Int. Cl.
*H04N 5/228* (2006.01)
(52) U.S. Cl.
USPC ..................................................... 348/208.4
(58) Field of Classification Search
None
See application file for complete search history.

(56) References Cited

U.S. PATENT DOCUMENTS

| | | | |
|---|---|---|---|
| 3,497,690 A | 2/1970 | Wheeless, Jr. et al. | 250/71 |
| 3,555,280 A | 1/1971 | Richards, Jr. | 250/201 |
| 3,586,760 A | 6/1971 | Dillenburger | 348/339 |
| 3,922,069 A | 11/1975 | Kishikawa et al. | 350/173 |
| 4,313,734 A | 2/1982 | Leuvering | 23/230 |
| 4,414,575 A | 11/1983 | Yamamoto et al. | 358/227 |
| 4,635,293 A | 1/1987 | Watanabe | 382/44 |
| 4,662,742 A | 5/1987 | Chupp | 356/39 |
| 4,677,680 A | 6/1987 | Harima et al. | 382/1 |
| 4,703,017 A | 10/1987 | Campbell et al. | 436/501 |
| 4,737,932 A | 4/1988 | Baba | 364/900 |
| 4,770,992 A | 9/1988 | Van den Engh et al. | 435/6 |
| 4,777,525 A | 10/1988 | Preston, Jr. | 358/102 |
| 4,786,165 A | 11/1988 | Yamamoto et al. | 356/23 |
| 4,845,197 A | 7/1989 | Petersen et al. | 530/387 |
| 4,857,453 A | 8/1989 | Ullman et al. | 435/7 |

(Continued)

FOREIGN PATENT DOCUMENTS

| | | | |
|---|---|---|---|
| EP | 0 154 404 | 9/1985 | G06F 15/68 |
| EP | 0 280 559 | 8/1988 | G01N 33/546 |

(Continued)

OTHER PUBLICATIONS

Amann et al., "Flourescent-Oligonucleotide Probing of Whole Cells for Determinative, Phylogenetic, and Environmental Studies in Microbiology," *Journal of Bacteriology* vol. 172, No. 2: 762-770, Feb. 1990.

(Continued)

*Primary Examiner* — Luong T Nguyen
(74) *Attorney, Agent, or Firm* — Lee & Hayes, PLLC

(57) ABSTRACT

A method to perform spatial alignment and spectral compensation for a multi-channel flow imaging system that acquires image data from a single imaging region is disclosed in U.S. Pat. No. 7,079,708. The spatial corrections disclosed therein are static, and do not vary unless the alignment of optical components in the imaging system or the specific detector are modified. However, when image data is acquired from two different imaging regions that are spaced apart along an axis of motion between the object being imaged and the imaging system, dynamic spatial offsets are induced between image data acquired from a first imaging region and image data acquired from a second, spaced apart imaging region. The dynamic spatial offsets are a function of an error in an estimated velocity of the object as it moves between the imaging regions, and may vary from object to object. Techniques for correcting dynamic spatial offsets are disclosed.

27 Claims, 16 Drawing Sheets

(56) References Cited

U.S. PATENT DOCUMENTS

| | | | |
|---|---|---|---|
| 5,096,807 A | 3/1992 | Leaback | 435/6 |
| 5,107,522 A | 4/1992 | Kitayama et al. | 375/97 |
| 5,122,453 A | 6/1992 | Martin et al. | 435/7.24 |
| 5,141,609 A | 8/1992 | Sweedler et al. | 204/180.1 |
| 5,153,916 A | 10/1992 | Inagaki et al. | 382/4 |
| 5,159,397 A | 10/1992 | Kosaka et al. | 356/73 |
| 5,159,398 A | 10/1992 | Maekawa et al. | 356/73 |
| 5,159,642 A | 10/1992 | Kosaka | 382/134 |
| 5,247,339 A | 9/1993 | Ogino | 356/73 |
| 5,247,340 A | 9/1993 | Ogino | 356/73 |
| 5,257,182 A | 10/1993 | Luck et al. | 364/413.1 |
| 5,272,354 A | 12/1993 | Kosaka | 250/574 |
| 5,351,311 A | 9/1994 | Rogers et al. | 382/45 |
| 5,372,936 A | 12/1994 | Fraatz et al. | 435/34 |
| 5,422,712 A | 6/1995 | Ogino | 356/73 |
| 5,436,144 A | 7/1995 | Stewart et al. | 435/91.2 |
| 5,444,527 A | 8/1995 | Kosaka | 356/73 |
| 5,459,240 A | 10/1995 | Foxwell et al. | 530/328 |
| 5,471,294 A | 11/1995 | Ogino | 356/73 |
| 5,547,849 A | 8/1996 | Baer et al. | 435/7.24 |
| 5,548,349 A | 8/1996 | Mizuguchi et al. | 348/766 |
| 5,548,395 A | 8/1996 | Kosaka | 356/73 |
| 5,568,315 A | 10/1996 | Shuman | 359/487 |
| 5,596,401 A | 1/1997 | Kusuzawa | 356/23 |
| 5,621,460 A | 4/1997 | Hatlestad et al. | 348/265 |
| 5,625,048 A | 4/1997 | Tsien et al. | 536/23.4 |
| 5,633,503 A | 5/1997 | Kosaka | 250/458.1 |
| 5,644,388 A | 7/1997 | Maekawa et al. | 356/73 |
| 5,674,743 A | 10/1997 | Ulmer | 435/287.2 |
| 5,686,960 A | 11/1997 | Sussman et al. | 348/335 |
| 5,695,934 A | 12/1997 | Brenner | 435/6 |
| 5,733,721 A | 3/1998 | Hemstreet, III et al. | 435/6 |
| 5,754,291 A | 5/1998 | Kain | 356/338 |
| 5,760,899 A | 6/1998 | Eismann | 356/326 |
| 5,764,792 A | 6/1998 | Kennealy | 382/133 |
| 5,784,162 A | 7/1998 | Cabib et al. | 356/456 |
| RE35,868 E | 8/1998 | Kosaka | 250/574 |
| 5,828,776 A | 10/1998 | Lee et al. | 382/133 |
| 5,831,723 A | 11/1998 | Kubota et al. | 356/73 |
| 5,844,670 A | 12/1998 | Morita et al. | 356/124 |
| 5,848,123 A | 12/1998 | Strommer | 378/98.8 |
| 5,855,753 A | 1/1999 | Trau et al. | 204/484 |
| 5,900,942 A | 5/1999 | Spiering | 356/400 |
| 5,926,283 A | 7/1999 | Hopkins | 356/419 |
| 5,929,986 A | 7/1999 | Slater et al. | 356/326 |
| 5,959,953 A | 9/1999 | Alon | 369/44.41 |
| 5,985,549 A | 11/1999 | Singer et al. | 435/6 |
| 5,986,061 A | 11/1999 | Pestka | 530/352 |
| 6,007,994 A | 12/1999 | Ward et al. | 435/6 |
| 6,007,996 A | 12/1999 | McNamara et al. | 435/6 |
| 6,014,468 A | 1/2000 | McCarthy et al. | 382/254 |
| 6,066,459 A | 5/2000 | Garini et al. | 435/6 |
| 6,108,082 A | 8/2000 | Pettipiece et al. | 356/301 |
| 6,115,119 A | 9/2000 | Sieracki et al. | 356/337 |
| 6,116,739 A | 9/2000 | Ishihara et al. | 353/31 |
| 6,156,465 A | 12/2000 | Cao et al. | 430/30 |
| 6,159,686 A | 12/2000 | Kardos et al. | 435/6 |
| 6,210,973 B1 | 4/2001 | Pettit | 436/172 |
| 6,211,955 B1 | 4/2001 | Basiji et al. | 356/336 |
| 6,229,913 B1 | 5/2001 | Nayar et al. | 382/154 |
| 6,249,314 B1 | 6/2001 | Yamamoto et al. | 348/242 |
| 6,249,341 B1 | 6/2001 | Basiji et al. | 356/73 |
| 6,256,096 B1 | 7/2001 | Johnson | 356/335 |
| 6,259,807 B1 | 7/2001 | Ravkin | 381/133 |
| 6,330,081 B1 | 12/2001 | Scholten | 358/463 |
| 6,330,361 B1 | 12/2001 | Mitchell et al. | 382/211 |
| 6,381,363 B1 | 4/2002 | Murching et al. | 382/164 |
| 6,473,176 B2 | 10/2002 | Basiji et al. | 356/336 |
| 6,507,391 B2 | 1/2003 | Riley et al. | 356/28 |
| 6,510,319 B2 | 1/2003 | Baum et al. | 455/442 |
| 6,519,355 B2 | 2/2003 | Nelson | 382/133 |
| 6,522,781 B1 | 2/2003 | Norikane et al. | 382/203 |
| 6,532,061 B2 | 3/2003 | Ortyn et al. | 356/28 |
| 6,548,259 B2 | 4/2003 | Ward et al. | 435/6 |
| 6,549,664 B1 | 4/2003 | Daiber et al. | 382/232 |
| 6,563,583 B2 | 5/2003 | Ortyn et al. | 356/400 |
| 6,580,504 B1 | 6/2003 | Ortyn et al. | 356/338 |
| 6,583,865 B2 | 6/2003 | Basiji et al. | 356/73 |
| 6,608,680 B2 | 8/2003 | Basiji et al. | 356/338 |
| 6,608,682 B2 | 8/2003 | Ortyn et al. | 356/419 |
| 6,618,140 B2 | 9/2003 | Frost et al. | 356/317 |
| 6,620,591 B1 | 9/2003 | Dunlay et al. | 435/7.2 |
| 6,658,143 B2 | 12/2003 | Hansen et al. | 382/133 |
| 6,671,044 B2 | 12/2003 | Ortyn et al. | 356/326 |
| 6,671,624 B1 | 12/2003 | Dunlay et al. | 702/19 |
| 6,707,551 B2 | 3/2004 | Ortyn et al. | 356/338 |
| 6,716,588 B2 | 4/2004 | Sammak et al. | 435/7.23 |
| 6,727,066 B2 | 4/2004 | Kaser | 435/6 |
| 6,763,149 B2 | 7/2004 | Riley et al. | 382/294 |
| 6,778,263 B2 | 8/2004 | Ortyn et al. | 356/28 |
| 6,873,733 B2 | 3/2005 | Dowski, Jr. | 382/232 |
| 6,875,973 B2 | 4/2005 | Ortyn et al. | 250/201.3 |
| 6,906,792 B2 | 6/2005 | Ortyn et al. | 356/28.5 |
| 6,927,922 B2 | 8/2005 | George et al. | 359/708 |
| 6,934,408 B2 | 8/2005 | Frost et al. | 382/129 |
| 6,947,128 B2 | 9/2005 | Basiji et al. | 356/73 |
| 6,947,136 B2 | 9/2005 | Ortyn et al. | 356/338 |
| 6,975,400 B2 | 12/2005 | Ortyn et al. | 356/419 |
| 7,006,710 B2 | 2/2006 | Riley et al. | 382/294 |
| 7,033,819 B2 | 4/2006 | Kim et al. | 435/29 |
| 7,042,639 B1 | 5/2006 | McDowell | 359/398 |
| 7,050,620 B2 | 5/2006 | Heckman | 382/133 |
| 7,057,732 B2 | 6/2006 | Jorgenson et al. | 356/445 |
| 7,079,708 B2 | 7/2006 | Riley et al. | 382/294 |
| 7,087,877 B2 | 8/2006 | Ortyn et al. | 250/201.2 |
| 7,139,415 B2 | 11/2006 | Finkbeiner | 382/128 |
| 7,180,673 B2 | 2/2007 | Dowski, Jr. | 359/637 |
| 7,190,832 B2 | 3/2007 | Frost et al. | 382/173 |
| 7,221,457 B2 | 5/2007 | Jorgenson et al. | 356/445 |
| 7,289,205 B2 | 10/2007 | Yaroslavsky et al. | 356/417 |
| 7,315,357 B2 | 1/2008 | Ortyn et al. | 356/73 |
| 7,450,229 B2 | 11/2008 | Ortyn et al. | 356/326 |
| 7,522,758 B2 | 4/2009 | Ortyn et al. | 382/133 |
| 7,567,695 B2 | 7/2009 | Frost et al. | 382/129 |
| 7,667,761 B2 | 2/2010 | Thomas | 348/335 |
| 8,269,843 B2 * | 9/2012 | Luo et al. | 348/208.4 |
| 8,310,671 B1 * | 11/2012 | Nguyen et al. | 356/301 |
| 2001/0006416 A1 | 7/2001 | Johnson | 356/73 |
| 2001/0012620 A1 | 8/2001 | Rich | 435/7.1 |
| 2002/0126275 A1 | 9/2002 | Johnson | 356/317 |
| 2002/0146734 A1 | 10/2002 | Ortyn et al. | 435/6 |
| 2003/0048931 A1 | 3/2003 | Johnson et al. | 382/128 |
| 2003/0049701 A1 | 3/2003 | Muraca | 435/7.23 |
| 2003/0059093 A1 | 3/2003 | Rosania et al. | 382/128 |
| 2003/0104439 A1 | 6/2003 | Finch | 435/6 |
| 2004/0093166 A1 | 5/2004 | Kil | 702/19 |
| 2004/0111220 A1 | 6/2004 | Ochs et al. | 702/19 |
| 2004/0241759 A1 | 12/2004 | Tozer et al. | 435/7.2 |
| 2005/0014129 A1 | 1/2005 | Cliffel et al. | 435/4 |
| 2006/0012797 A1 * | 1/2006 | Chang et al. | 356/484 |
| 2006/0246481 A1 | 11/2006 | Finch et al. | 435/6 |
| 2006/0257884 A1 | 11/2006 | Brawley et al. | 435/6 |
| 2007/0054350 A1 | 3/2007 | Walker, Jr. | 435/34 |
| 2008/0240539 A1 | 10/2008 | George et al. | 382/133 |
| 2009/0202130 A1 | 8/2009 | George et al. | 382/133 |

FOREIGN PATENT DOCUMENTS

| | | | |
|---|---|---|---|
| EP | 0 281 327 | 6/1993 | G01N 33/546 |
| EP | 0 372 707 | 3/1996 | C07K 14/00 |
| EP | 0 950 890 | 10/1999 | G01N 15/14 |
| EP | 1 316 793 | 6/2003 | |
| WO | WO 88/08534 | 11/1988 | G01N 33/543 |
| WO | WO 90/10715 | 9/1990 | C12Q 1/68 |
| WO | WO 95/20148 | 7/1995 | G01N 21/64 |
| WO | WO 97/26333 | 7/1997 | C12N 15/12 |
| WO | WO 98/53093 | 11/1998 | C12Q 1/00 |
| WO | WO 98/53300 | 11/1998 | G01N 21/00 |
| WO | WO 99/24458 | 5/1999 | C07K 1/10 |
| WO | WO 99/64592 | 12/1999 | |
| WO | WO 00/06989 | 2/2000 | |
| WO | WO 00/14545 | 3/2000 | G01N 33/58 |
| WO | WO 00/42412 | 7/2000 | G01N 15/02 |
| WO | WO 01/11341 | 2/2001 | G01N 15/14 |

(56) References Cited

FOREIGN PATENT DOCUMENTS

| WO | WO 01/46675 | 6/2001 | ............ G01N 15/14 |
|---|---|---|---|
| WO | WO 02/17622 | 2/2002 | ............ H04N 5/232 |
| WO | WO 02/18537 | 3/2002 | |
| WO | WO 2002/031182 | 4/2002 | |
| WO | WO 02/35474 | 5/2002 | ............ G06T 7/00 |
| WO | WO 02/073200 | 9/2002 | ............ G01N 33/53 |
| WO | WO 02/079391 | 10/2002 | |
| WO | WO 2005/090945 | 9/2005 | ............ G01N 15/14 |
| WO | WO 2005/098430 | 10/2005 | ............ G01N 33/50 |

OTHER PUBLICATIONS

Arkesteijn et al., "Chromosome Specific DNA Hybridization in Suspension for Flow Cytometric Detection of Chimerism in Bone Marrow Transplantation and Leukemia," *Cytometry* 19: 353-360, Apr. 1995.

Bains et al., "Flow Cytometric Quantitation of Sequence-Specific nRNA in Hemopoietic Cell Suspension by Primer-Induced *in Situ* (PRINS) Fluorescent Nucleotide Labeling," *Experimental Cell Research* 208: 321-326, Sep. 1993.

Barren III et al., "Method for Identifying Prostate Cells in Semen Using Flow Cytometry," *The Prostate* 36: 181-188, 1998.

Bauman et al., "Flow Cytometric Detection of Ribosomal RNA in Suspended Cells by Fluorescent In Situ Hybridization," *Cytometry* 9: 517-524, 1988.

Baumgartner et al., "Automated Evaluation of Frequencies of Aneuploid Sperm by Laser-Scanning Cytometry (LSC)," *Cytometry* 44: 156-160, 2001.

Ben-Eliezer et al., "All-optical extended depth of field imaging system," *Journal of Optics A: Pure and Applied Optics* 5: S164-S169, 2003.

Biggs et al., "Acceleration of iterative image restoration algorithms" *Applied Optics* vol. 36, No. 8: 1766-1775, Mar. 10, 1997.

Boyle et al., "Isolation and Initial Characterization of a Large Repeat Sequence Element Specific to Mouse Chromosome 8," *Genomics* vol. 12, No. 3: 517-525, 1992.

Callet-Bauchu et al., "Distribution of the cytogenetic abnormality +i(3)(q10) in persistent polyclonal B-cell lymphocytosis: a FICTION study in three cases," *British Journal of Haematology* 99: 531-536, Dec. 1997.

Ding et al., "Characterization and Quantitation of NF-$_\kappa$B Nuclear Translocation Induced by Interleukin-1 and Tumor Necrosis Factor-α," *The Journal of Biological Chemistry* vol. 273, No. 44: 28897-28905, Oct. 30, 1998.

Disteche et al., "Isolation and characterization of two repetitive DNA fragments located near the centromere of the mouse X chromosome," *Cytogenetics and Cell Genetics* 39: 262-268, 1985.

Engvall, Eva. "Enzyme Immunoassay ELISA and EMIT," *Methods in Enzymology* vol. 70, Part A: 419-439, 1980.

Fernandez-Lago et al., "Fluorescent Whole-Cell Hybridization with 16S rRNA-Targeted Oligonucleotide Probes to Identify *Brucella* spp. by Flow Cytometry," *Journal of Clinical Microbiology* vol. 38, No. 7: 2768-2771, Jul. 2000.

Ferraro et al., "Extended focused image in microscopy by digital holography." *Optics Express*, vol. 13, No. 18: 6738-6749, 2005.

George et al., "Extended depth of field using a logarithmic asphere" *Journal of Optics A: Pure and Applied Optics* 5: S157-S163, 2003.

George et al., "Distinguishing Modes of Cell Death Using the ImageStream® Multispectral Imaging Flow Cytometer," *Cytometry Part A* 59A: 237-245, 2004.

George et al., "Quantitative measurement of nuclear translocation events using similarity analysis of multispectral cellular images obtained in flow," *Journal of Immunological Methods* 311: 117-129, 2006.

Gordy et al., "Visualization of Antigen Presentation by Actin-Mediated Targeting of Glycolipid-Enriched Membrane Domains to the Immune Synapse of B cell APCs." *Journal of Immunology* vol. 172, No. 4: 2030-2038, Feb. 15, 2004.

Hultdin et al., "Telomere analysis by fluorescence in situ hybridization and flow cytometry," *Nucleic Acids Research* vol. 26, No. 16: 3651-3656, Aug. 15, 1998.

Kubota et al., "Flow Cytometer and Imaging Device Used in Combination." *Cytometry* 21: 129-132, 1995.

Kubota, Fumio. "Analysis of red cell and platelet morphology using an imaging-combined flow cytometer." *Clin. Lab. Haem.* 25: 71-76, 2003.

Lauzon et al., "Flow Cytometric Measurement of Telomere Length," *Cytometry* 42: 159-164, Jun. 2000.

Levron et al., "Sperm chromosome abnormalities in men with severe male factor infertility who are undergoing in vitro fertilization with intracytoplasmic sperm injection," *Fertility and Sterility* vol. 76, No. 3: 479-484, Sep. 2001.

Lowe et al., "Aneuploid epididymal sperm detected in chromosomally normal and Robertsonian translocation-bearing mice using a new three-chromosome FISH method," *Chromosoma* 105: 204-210, 1996.

Majno et al., "Apoptosis, Oncosis, and Necrosis *An Overview of Cell Death*," *American Journal of Pathology* vol. 146, No. 1: 3-15, Jan. 1, 1995.

Martin et al., "Detection of aneuploidy in human interphase spermatozoa by fluorescence in situ hybridization (FISH)," *Cytogenetics and Cell Genetics* 64: 23-26, 1993.

Nautiyal et al., "17β-Estradiol induces nuclear translocation of CrkL at the window of embryo implantation," *Biochemical and Biophysical Research Communications* 318: 103-112, 2004.

Oberholzer et al., "Methods in quantitative image analysis." *Histochem Cell Biol*, vol. 105: 333-355, 1996.

Ong, Sim Heng, "Development of a System for Imaging and Classifying Biological Cells in a Flow Cytometer," Doctor of Philosophy Thesis, University of Sydney, School of Electrical Engineering, Aug. 1985.

Ong et al., "Development of an Image Flow Cytometer," *Analytical and Quantitative Cytology and Histology*. XIVth International Conference on Medical and Biological Engineering and the VIIth International Conference on Medical Physics, Finland: 375-382, Aug. 1987.

Ong et al., "Optical Design in a Flow System for Imaging Cells," *Sciences in Medicine*, vol. 14, No. 2: 74-80, 1991.

Ong et al., "Analysis of MTF Degradation in the Imaging of Cells in a Flow System," *International Journal of Imaging Systems & Technology* 5: 243-250, 1994.

Ortyn et al., "Extended Depth of Field Imaging for High Speed Cell Analysis" *Cytometry Part A* 71A: 215-231, 2007.

Pala et al., "Flow cytometric measurement of intracellular cytokines," *Journal of Immunological Methods* 243: 107-124, 2000.

Pang et al., "Detection of aneuploidy for chromosomes 4, 6, 7, 8, 9, 10, 11, 12, 13, 17, 18, 21, X and Y by fluorescence in-situ hybridization in spermatozoa from nine patients with oligoasthenoteratozoospermia undergoing intracytoplasmic sperm injection," *Human Reproduction* vol. 14, No. 5: 1266-1273, 1999.

Patterson et al., "Detection of HIV-1 DNA and Messenger RNA in Individual Cells by PCR-Driven in Situ Hybridization and Flow Cytometry," *Science* 260: 976-979, May 14, 1993.

Perreault et al., "The Role of Disulfide Bond Reduction during Mammalian Sperm Nuclear Decondensation in Vivo," *Developmental Biology* 101: 160-167, 1984.

Pinkel et al., "Cytogenetic analysis using quantitative, high sensitivity, fluorescence hybridization," *Proceedings of the National Academy of Sciences: Genetics* 83: 2934-2938, 1986.

Pollice et al., "Sequential Paraformaldehyde and Methanol Fixation for Simultaneous Flow Cytometric Analysis of DNA, Cell Surface Proteins, and Intracellular Proteins," *Cytometry* 13: 432-444, 1992.

Ried et al., "Simultaneous visualization of seven different DNA probes by in situ hybridization using combinatorial fluorescence and digital imaging microscopy," *Proceedings of the National Academy of Sciences: Genetics* 89: 1388-1392, Feb. 1992.

Robbins et al., "Detection of Aneuploid Human Sperm by Fluorescence In Situ Hybridization: Evidence for a Donor Difference in Frequency of Sperm Disomic for Chromosomes I and Y," *The American Journal of Human Genetics*, 52: 799-807, 1993.

(56) References Cited

OTHER PUBLICATIONS

Robbins et al., "Three-probe Fluorescence in situ Hybridization to Assess Chromosome X, Y, and 8 Aneuploidy in Sperm of 14 Men from Two Healthy Groups: Evidence for a Paternal Age Effect on Sperm Aneuploidy," *Reproduction, Fertility and Development* 7: 799-809, 1995.

Robbins et al., "Use of Fluorescence in Situ Hybridization (FISH) to Assess Effects of Smoking, Caffeine, and Alcohol on Aneuploidy Load in Sperm of Healthy Men," *Environmental and Molecular Mutagenesis* 30: 175-183, 1997.

Rufer et al., "Telomere length dynamics in human lymphocyte subpopulations measured by flow cytometry," *Nature Biotechnology* 16: 743-747, Aug. 1998.

Salzman et al., "Light Scatter: Detection and Usage," Current Protocols in *Cytometry* Supplement 9: 1.13.1-1.138.8, 1999.

Satoh et al., "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry* 48: 194-201, 2002.

Schmid et al., "Evaluation of inter-scorer and inter-laboratory reliability of the mouse epididymal sperm aneuploidy (m-ESA) assay," *Mutagenesis* vol. 16, No. 3: 189-195, 2001.

Schmid et al., "Simultaneous Flow Cytometric Analysis of Two Cell Surface Markers, Telomere Length, and DNA Content," *Cytometry* 49: 96-105, 2002.

Shi et al., "Aneuploidy in human sperm: a review of the frequency and distribution of aneuploidy, effects of donor age and lifestyle factors," *Cytogenetics and Cell Genetics* 90: 219-226, 2000.

Timm et al., "Amplification and Detection of a Y-Chromosome DNA Sequence by Fluorescence In Situ Polymerase Chain Reaction and Flow Cytometry Using Cells in Suspension," *Cytometry (Communications in Clinical Cytometry)* 22: 250-255, 1995.

Trask et al., "Fluorescence in situ hybridization to interphase cell nuclei in suspension allows flow cytometric analysis of chromosome content and microscopic anaylsis of nuclear organization," *Human Genetics* 78:251-259, 1988.

Tucker et al., "Extended depth of field and aberration control for inexpensive digital microscope systems" *Optics Express* vol. 4, No. 11: 467-474, May 24, 1999.

van den Berg et al., "Detection of Y Chromosome by In situ Hybridization in Combination with Membrane Antigens by Two-Color Immunofluorescence," *Laboratory Investigation* vol. 64, No. 5: 623-628, 1991.

Wang et al., "A Novel Apoptosis Research Method With Imaging-Combined Flow Cytometer and HITC OR IR-125 Staining," *Cytometry (Clinical Cytometry)* 50: 267-274, 2002.

Weber-Matthieson et al., "Rapid immunophenotypic characterization of chromosomally aberrant cells by the new FICTION method," *Cytogenetics Cell Genetics* 63: 123-125, 1993.

Weber-Matthieson et al., "Simultaneous Fluorescence Immunophenotyping and Interphase Cytogenetics: A Contribution to the Characterization of Tumor Cells," *Journal of Histochemistry and Cytochemistry* vol. 40, No. 2: 171-175, 1992.

Wietzorrek et al., "A New Multiparameter Flow Cytometer: Optical and Electrical Cell Analysis in Combination With Video Microscopy in Flow," *Cytometry* 35: 291-301, 1999.

Wyrobek et al., "Detection of Sex Chromosomal Aneuploidies X-X, Y-Y, and X-Y, in Human Sperm Using Two-Chromosome Fluorescence In Situ Hybridization," *American Journal of Medical Genetics* 53: 1-7, 1994.

Wyrobek et al., "Fluorescence In Situ Hybridization to Y Chromosomes in Decondensed Human Sperm Nuclei," *Molecular Reproduction and Development* 27: 200-208, 1990.

Robbins et al., "Aneuploidy in sperm of Hodgkin's disease patients receiving NOVP chemotherapy," The American Journal of Human Genetics vol. 55, No. 3—Supplement: A68 (371), Sep. 1994.

Schwerin et al., "Quantification of Y Chromosome Bearing Spermatozoa of Cattle Using In Situ Hybridization," Molecular Reproduction and Development 30: 39-43, 1991.

Timm et al., "Fluorescent In Situ Hybridization En Suspension (FISHES) Using Digoxigenin-Labeled Probes and Flow Cytometry," Biotechniques vol. 12, No. 3: 362-367, 1992.

van Dekken et al., "Flow Cytometric Quantification of Human Chromosome Specific Repetitive DNA Sequences by Single and Bicolor Fluorescent In Situ Hybridization to Lymphocyte Interphase Nuclei," Cytometry 11: 153-164, 1990.

Wyrobek et al., "Smokers produce more aneuploid sperm than non-smokers," The American Society of Human Genetics, 45th Annual Meeting, A131: 737, Oct. 24-28, 1995.

Dragowska et al., "Measurement of DNA repeat sequence by flow cytometry," Cytometry Supplement 7: 51, Oct. 1994.

Hecht, Eugene. "Optics 4th ed., Light in Bulk Matter" Addison-Wesley Longman, Inc., XP-002465391.

\* cited by examiner

*MULTIPLE CAMERAS WITH DEDICATED FILTERS*

*SINGLE CAMERA WITH STACKED FILTERS*

ILLUSTRATION OF CROSSTALK IN MULTICHANNEL IMAGING SYSTEM

OVERALL ALGORITHM STRUCTURE

| | Ch01 | Ch02 | Ch03 | Ch04 | Ch05 | Ch06 | Ch07 | Ch08 | Ch09 | Ch10 | Ch11 | Ch12 |
|---|---|---|---|---|---|---|---|---|---|---|---|---|
| Vertical | -0.12 | -0.14 | -0.22 | -0.24 | 0.00 | -0.07 | -0.16 | -0.08 | -0.26 | -0.09 | 0.00 | -0.06 |
| Horizontal | 0.02 | 0.13 | 0.03 | 0.04 | 0.00 | -0.04 | -0.08 | 0.19 | 0.04 | 0.27 | 0.00 | 0.08 |

FIG. 13A (TABLE 1)

*FIG. 13B (TABLE 2)*

SPATIAL ALIGNMENT OF IMAGE DATA FROM A MULTICHANNEL DETECTOR USING A REFERENCE IMAGE

RELATED APPLICATIONS

This application is based on a prior copending provisional application Ser. No. 61/331,760, filed on May 5, 2010, the benefit of the filing date of which is hereby claimed under 35 U.S.C. §119(e).

BACKGROUND

Multi-channel imaging systems, such as the systems disclosed in U.S. Pat. No. 6,211,955 (the disclosure and drawings of which are specifically incorporated herein by reference) can be used to acquire multi-spectral images of an object (such as a cell). Such systems often have some amount of spectral crosstalk (leakage) across different spectral channels, particularly where there is some mismatch between the spectral widths of each channel (an exemplary channel might span 50 nm) and the spectral emission of fluorescent dyes (an exemplary spectral emission might have a peak spanning about 50 nm and a tail extending for up to another 100 nm) used to tag the cells. In order to obtain accurate spectral data in each channel, it is necessary to compensate the data for this leakage. When dealing with image data, proper compensation requires that the images in the different channels be registered to sub-pixel precision before the compensation routine can be applied. U.S. Pat. No. 7,079,708 (the disclosure and drawings of which are specifically incorporated herein by reference) describes a method to accomplish crosstalk reduction in a system where the multi-spectral images are acquired from the same imaging region. That reference discloses a method to pre-compute X and Y spatial offsets and spectral leakage coefficients between different channels on a multi-channel instrument, which can then be applied to acquired data to accurately align and spectrally compensate the images of the object in each channel. The method disclosed therein supposes that the spatial offsets between channels are a function of the instrument setup, an assumption that is valid for an imaging system where all the image data is acquired from the same imaging region. This type of spatial offset can be considered to be a static spatial offset, because unless the instrument set up is modified (i.e., the alignments of the optical components are changed or the detector is replaced), once computed the spatial offsets will remain unchanged.

However, applicants have discovered that when image data is acquired from two spatially distinct imaging regions at different times (where the two imaging regions are spaced apart along an axis of motion between the imaging system and the object being imaged), there may exist a spatial offset between images acquired in the first imaging region and images acquired at a later time in the second region, where the cross region spatial offset is a function of an error in an estimated speed of the object as it moves between the two different locations. Significantly, because the cross region spatial offset is not a function of the parameters of the imaging system, but rather a function of the speed of the object being imaged, the spatial offset correction technique disclosed in U.S. Pat. No. 7,079,708 cannot correct for the cross region spatial offset. Left uncorrected, the cross region spatial offset degrades the quality of the data collected. This cross region spatial offset can be considered to be a dynamic spatial offset, because the offset can change from object to object, as different objects may be moving at different speeds.

It would be desirable to provide techniques for correcting for cross region spatial offsets between images acquired from spatially separated imaging regions, where such offsets are directly related to an error in an estimated speed of the object as it moves between the two spatially separated imaging regions.

SUMMARY

This application specifically incorporates by reference the disclosures and drawings of each patent application and issued patent identified above as a related application.

The concepts disclosed herein encompass a technique to spatially align images taken from two different locations at two different times, where the cross region spatial offset is a function of an error in an estimated speed of the object as it moves between the two different locations.

In at least one embodiment, the technique is applied to multi-channel imaging, where there might be more than one object in each image, and where the cross region spatial offset is corrected for each different object (as the different objects could be moving at different speeds, such that the magnitude of the cross region spatial offset might be different for different objects).

In at least one embodiment, the technique is applied to imaging systems where a first camera is used to acquire an image (or a plurality of images) of the object from a first imaging region, and a second camera is used to acquire an image (or a plurality of images) of the object from a second imaging region, where the first and second imaging regions are spaced apart along an axis of motion between the cameras and the object (in some embodiments, the object is in motion, while in other embodiments, the cameras (whose positions are fixed relative to each other) are in motion).

In at least one embodiment, the technique is applied to imaging systems where a single camera having a relatively large field of view is used to acquire an image (or a plurality of images) of the object from a first portion of the field of view (i.e., a first imaging region) and from a second portion of the field of view (i.e., a second imaging region), where the first and second portions (imaging regions) are spaced apart along an axis of motion between the camera and the object (in some embodiments, the object is in motion, while in other embodiments, the camera is in motion). In an exemplary embodiment, each field of view about 50 microns in height.

An exemplary (but not limiting) method for implementing the concepts disclosed herein, for correcting dynamic spatial alignment errors in a multi-channel imaging system that acquires multi-channel images of an object from at least two spatially distinct imaging regions at different times, while there is relative motion between the object and each imaging region, includes the following steps: (a) acquiring multi-channel images of an object from a first imaging region, thereby acquiring a first set of images; (b) acquiring multi-channel images of an object from a second imaging region after acquisition of the first set of images, thereby acquiring a second set of images, the first imaging region and the second imaging region being spatially separated, where acquisition of the multi-channel images of the object from the second imaging region is based on an estimated speed of the relative motion between the object and each imaging region; (c) using first predetermined offset data corresponding to the first imaging region to spatially align each image in the first set of images; (d) using second predetermined offset data corresponding to the second imaging region to spatially align each image in the second set of images; (e) determining a cross region spatial misalignment between the first set of images and the second set of images by analyzing image data from the first and second set of images, where the cross region spatial misalignment is proportional to an error in the estimated speed; and (f) correcting the cross region spatial misalignment to spatially align the first set of images with the second set of images.

Where there is a likelihood of significant spectral crosstalk in the reference images from the first and second sets of images, such spectral crosstalk should be minimized before using the reference images to determine the cross region spatial misalignment between the first and second sets of images (because such spectral crosstalk will make the determination of the degree of the cross region spatial misalignment difficult). Thus, in an exemplary embodiment, after the steps of using the first predetermined offset data to align each image in the first set of images and using the second predetermined offset data to align each image in the second set of images, and before implementing the steps of determining and correcting the cross region spatial alignment, the method involves performing the steps of correcting spectral crosstalk in the first set of images, and correcting spectral crosstalk in the second set of images. In at least some embodiments, the spectral crosstalk is reduced in a first brightfield reference channel image from the first set of images, and in a second brightfield reference channel image from the second set of images. Then, the step of determining the cross region spatial misalignment is based on determining a spatial misalignment between the first brightfield reference channel image and the second brightfield reference channel image.

It should be recognized that the concepts disclosed herein encompass embodiments where the first set of images from the first imaging region are acquired using a first imaging component and the second set of images from the second imaging region are acquired using a different imaging component, as well as embodiments where the first and second sets of images are acquired using a single imaging component having a field of view sufficiently large to enable the different sets of images to be obtained from spatially distinct imaging regions.

It should also be recognized that in at least some embodiments, the image data from the first imaging region and the image data from the second imaging region are acquired using time delay integration, to enhance a signal to noise ratio of such image data.

In addition to the method discussed above in detail, it should be understood that the concepts disclosed herein also encompass imaging systems including a processor implementing such a method, as well as non-transient memory media storing machines instructions for implementing such a method.

While the concepts disclosed herein are particularly useful for correcting cross region spatial misalignment between two sets of images acquired from spatially distinct imaging regions, where each set of images includes multi-channel images, the concepts disclosed herein can also be applied to image data where only one image is acquired from a first imaging region, and one image is acquired from a second imaging region spaced apart from the first imaging region, to enable cross region spatial misalignment between the first and second images to be corrected, where such cross region spatial misalignment is a function of an error in an estimated speed of the object moving between the two imaging regions.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 4:
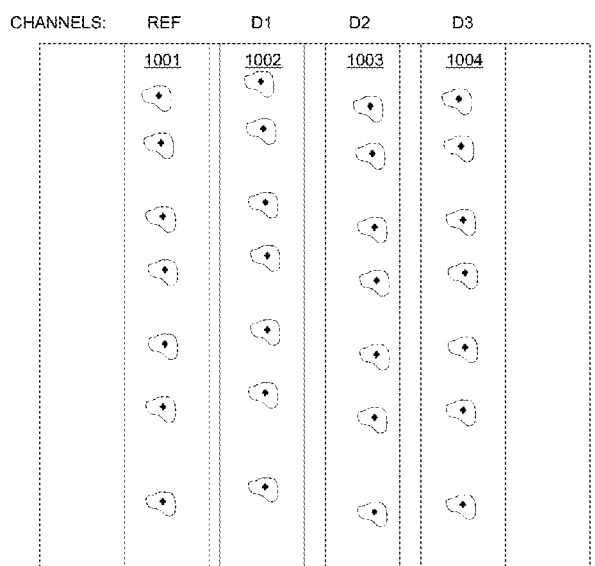
Figure 3:
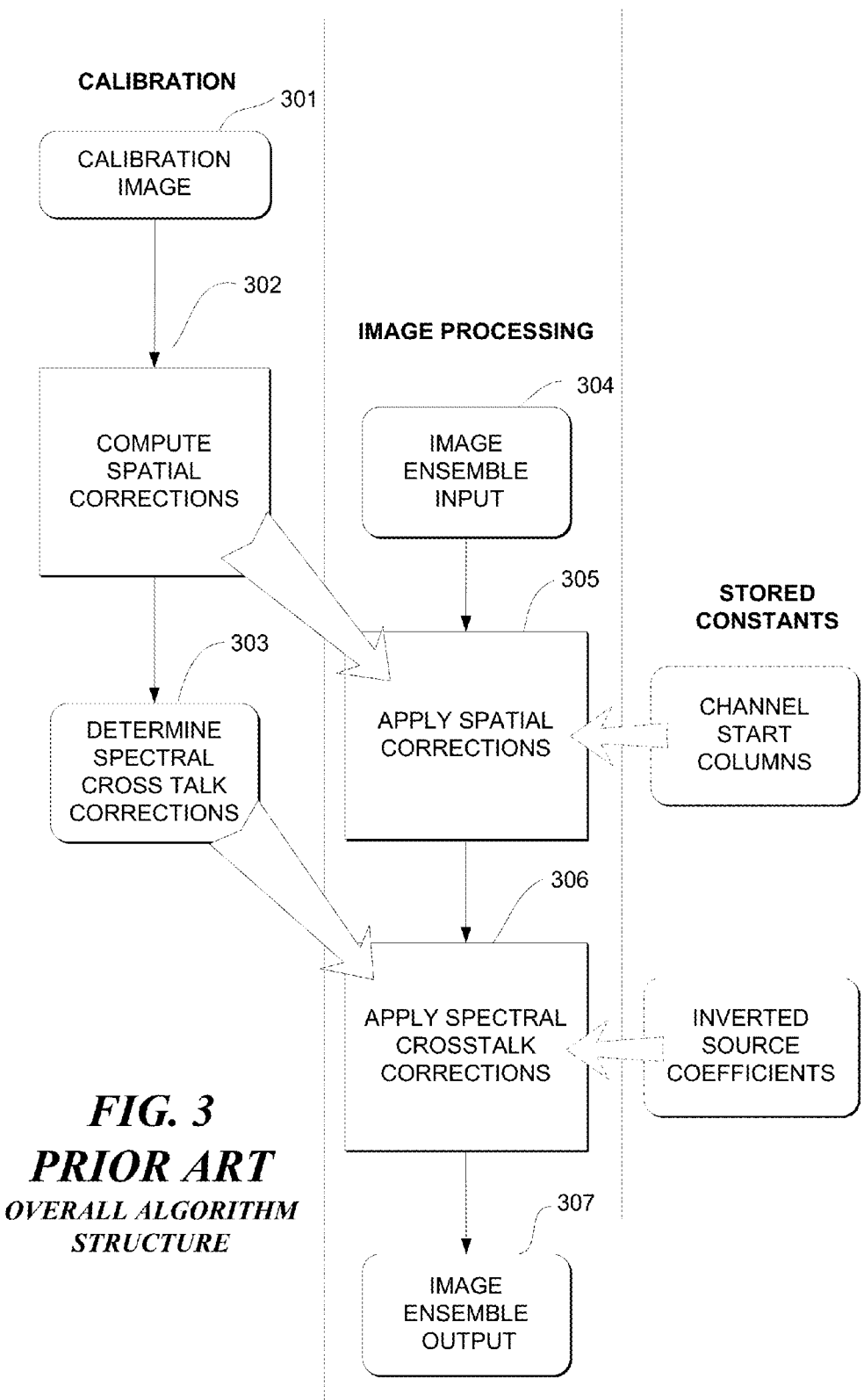
Figure 5A:
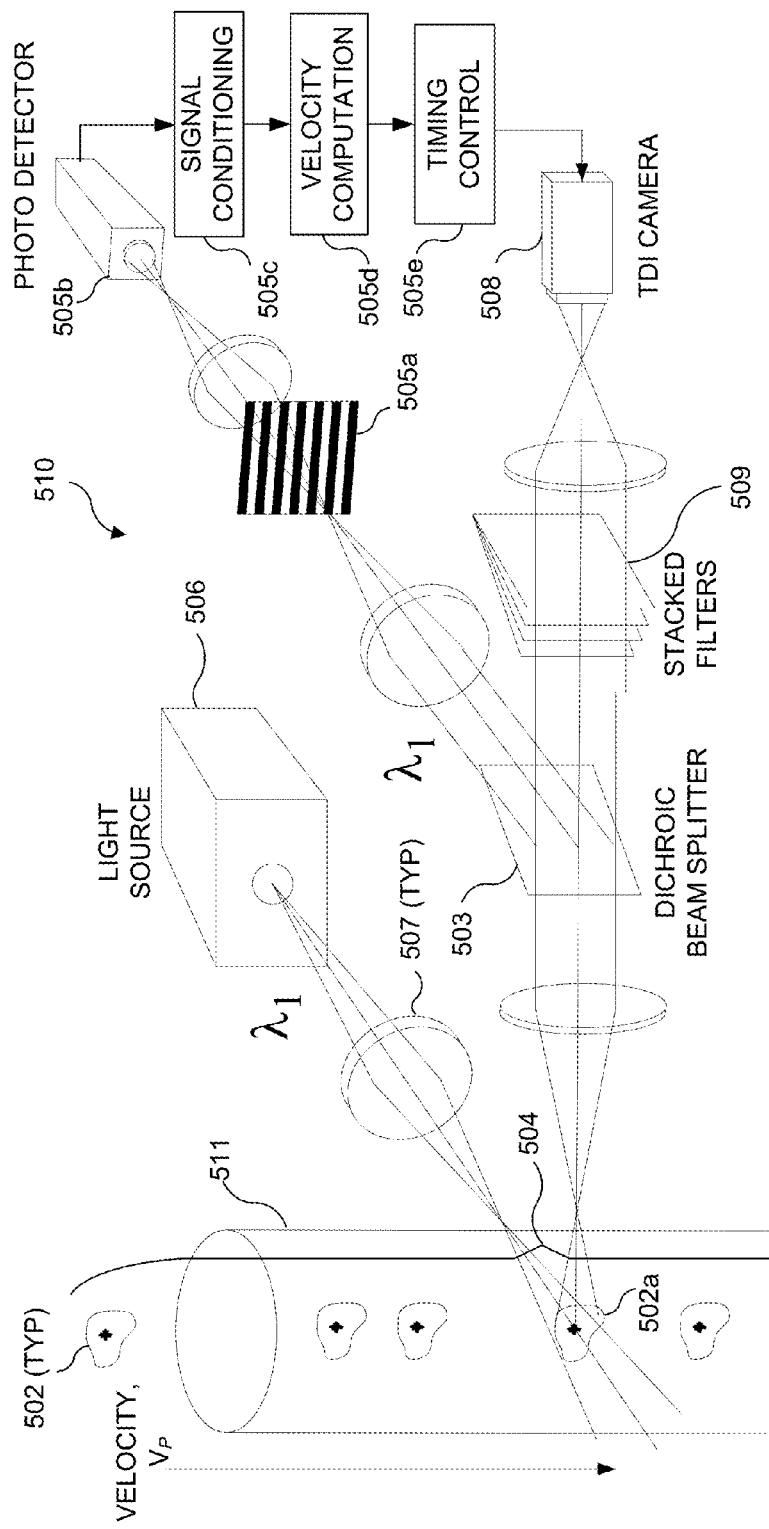
Figure 5B:
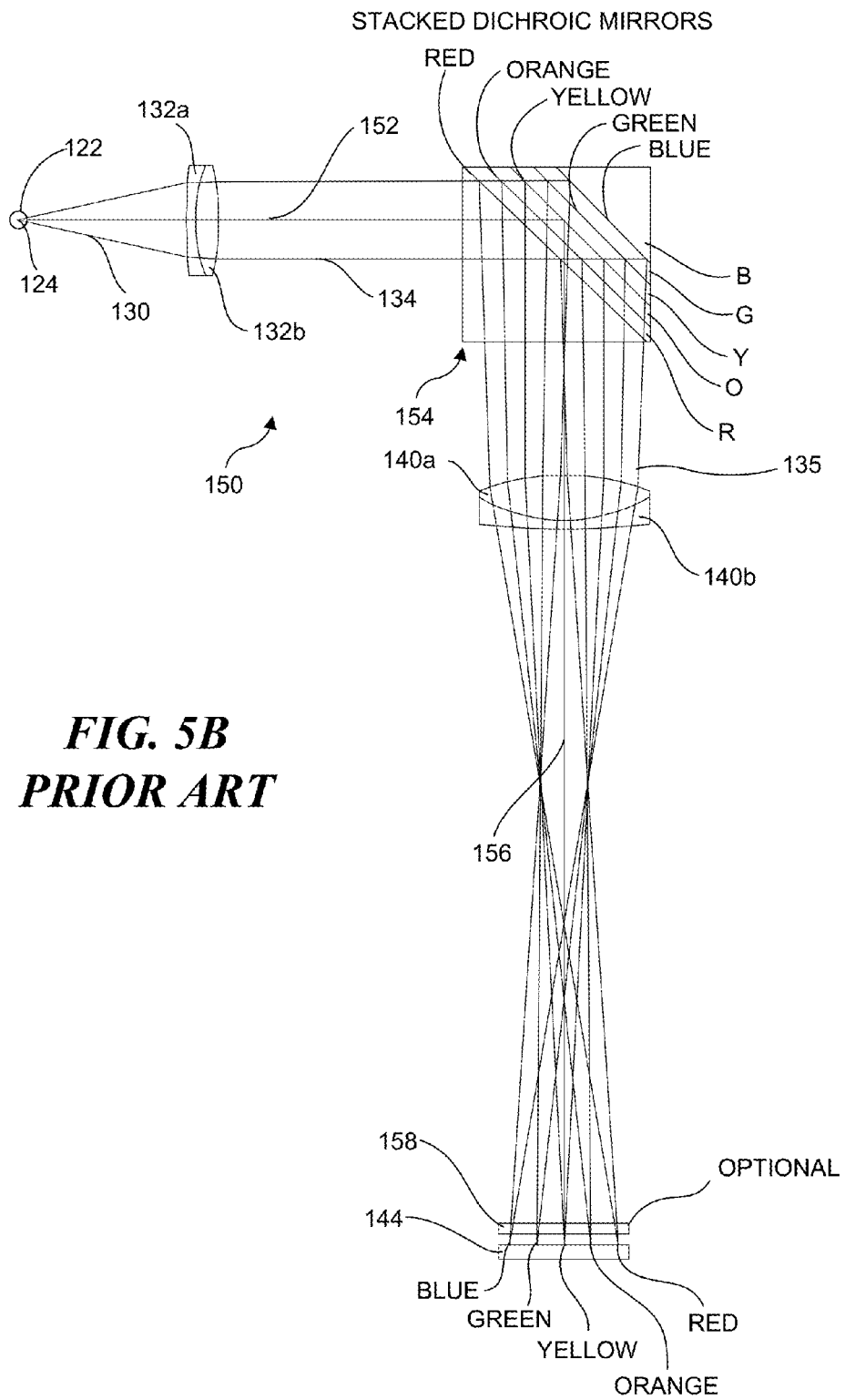
Figure 5C:
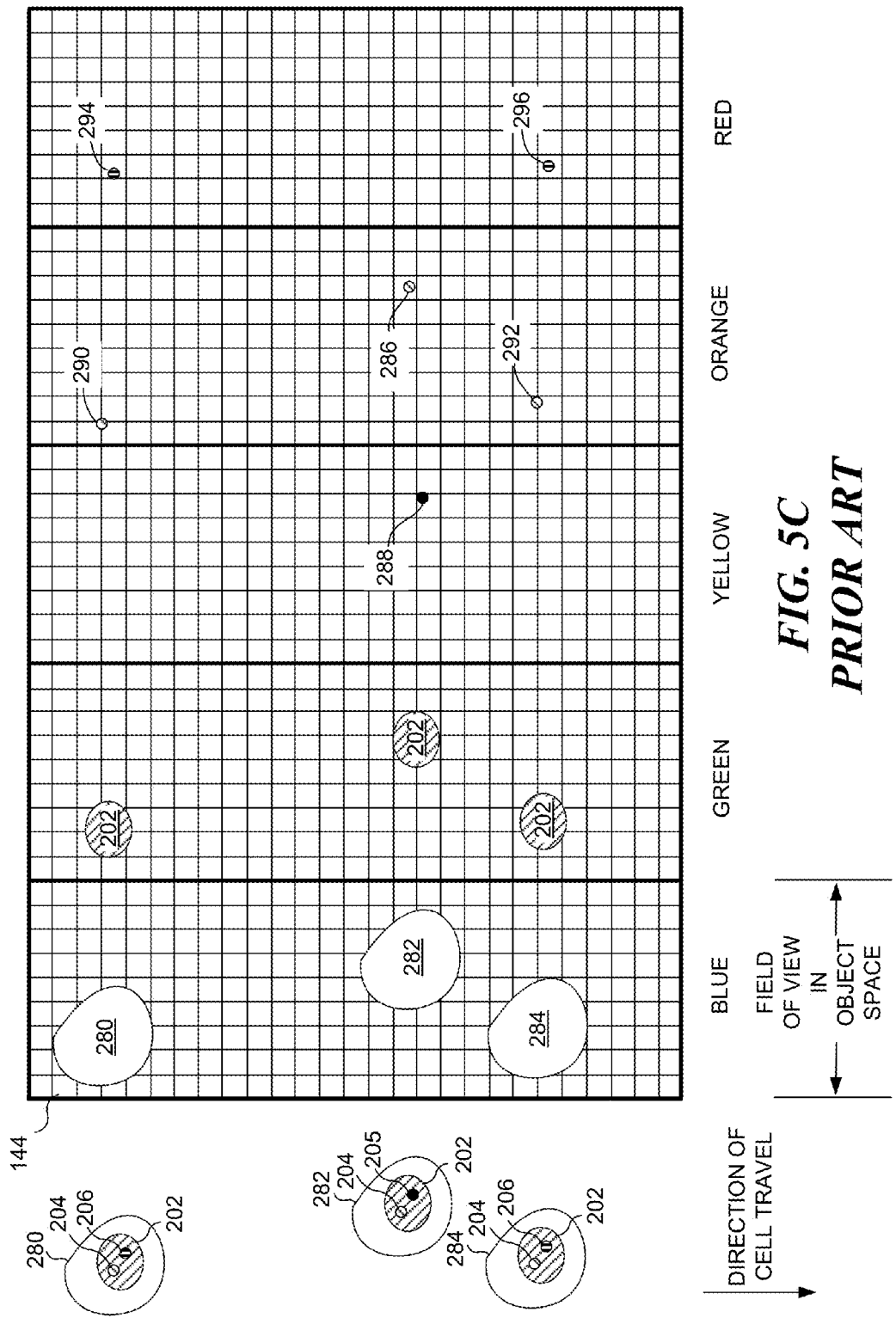
Figure 6:
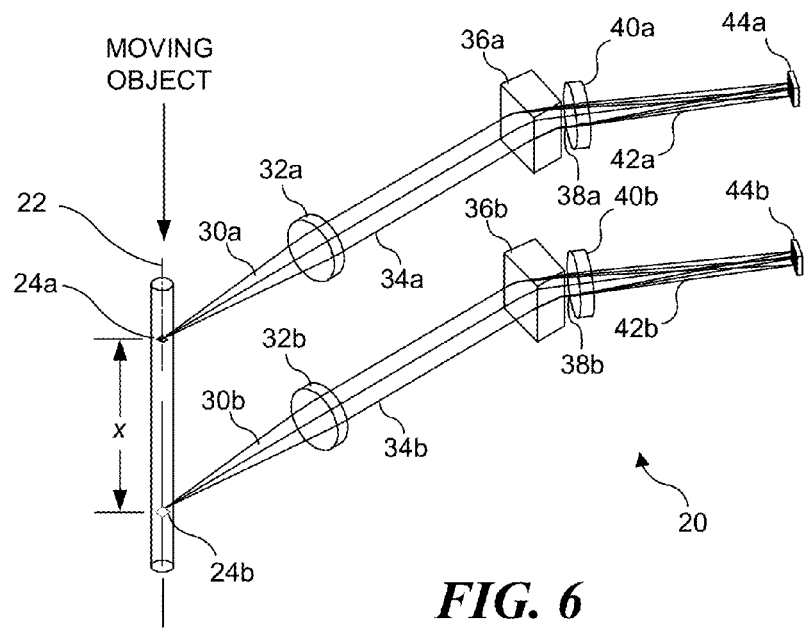
Figure 7:
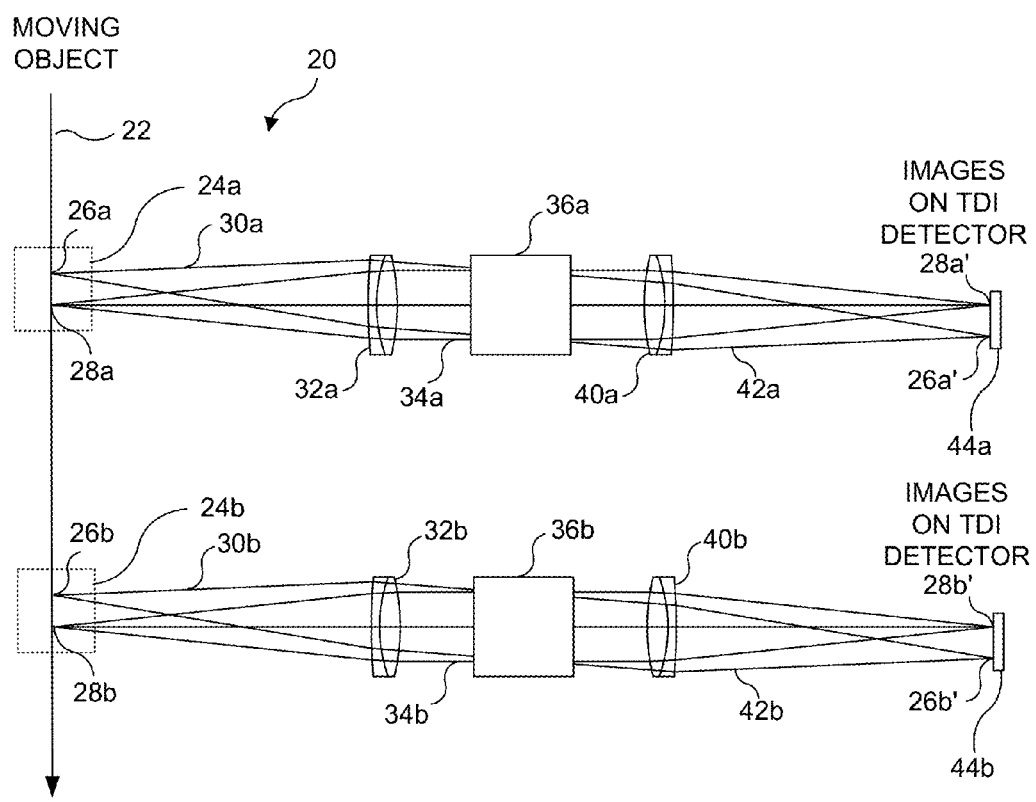
Figure 8:
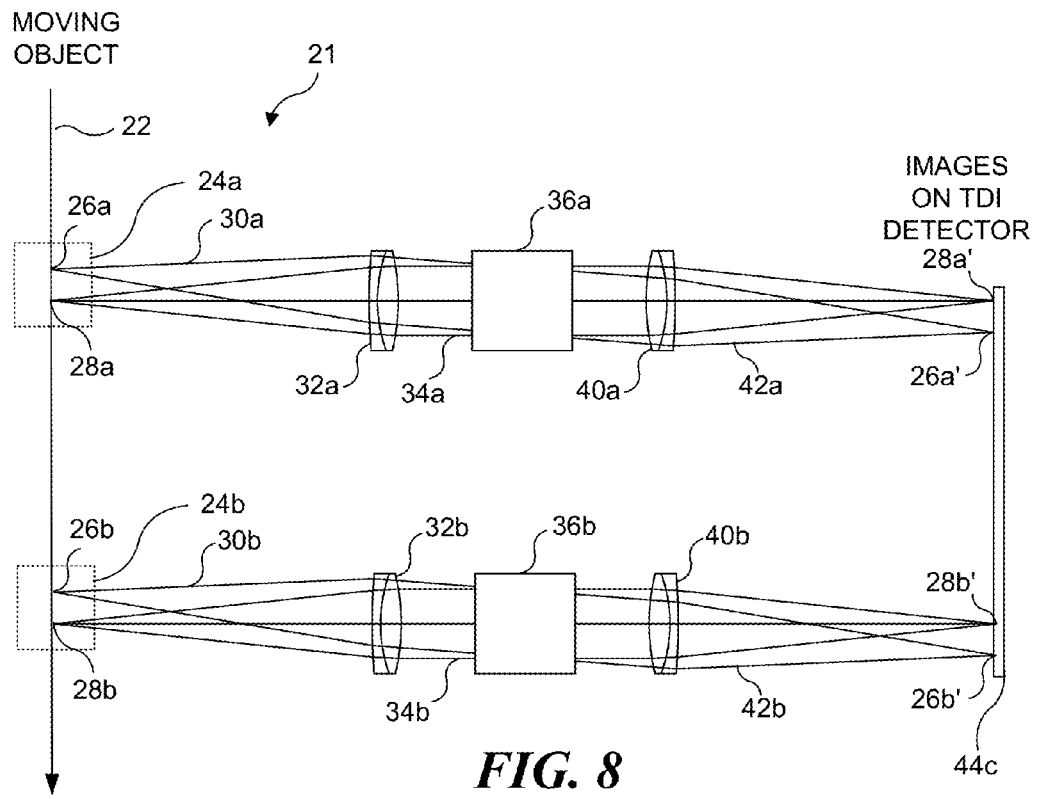
Figure 9:
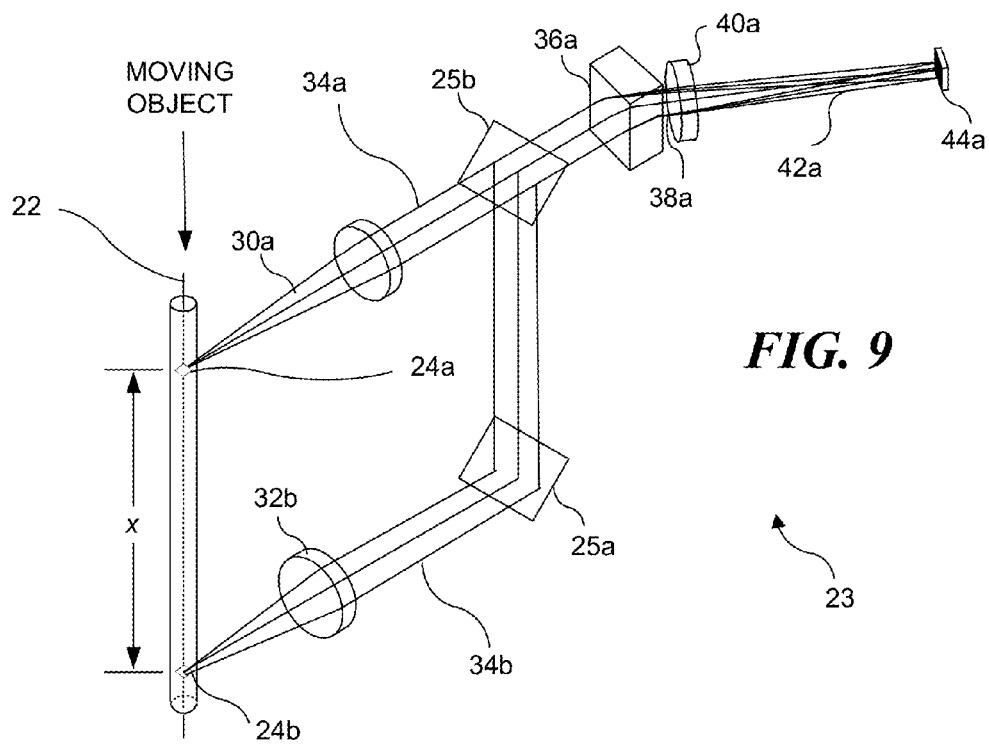
Figure 10:
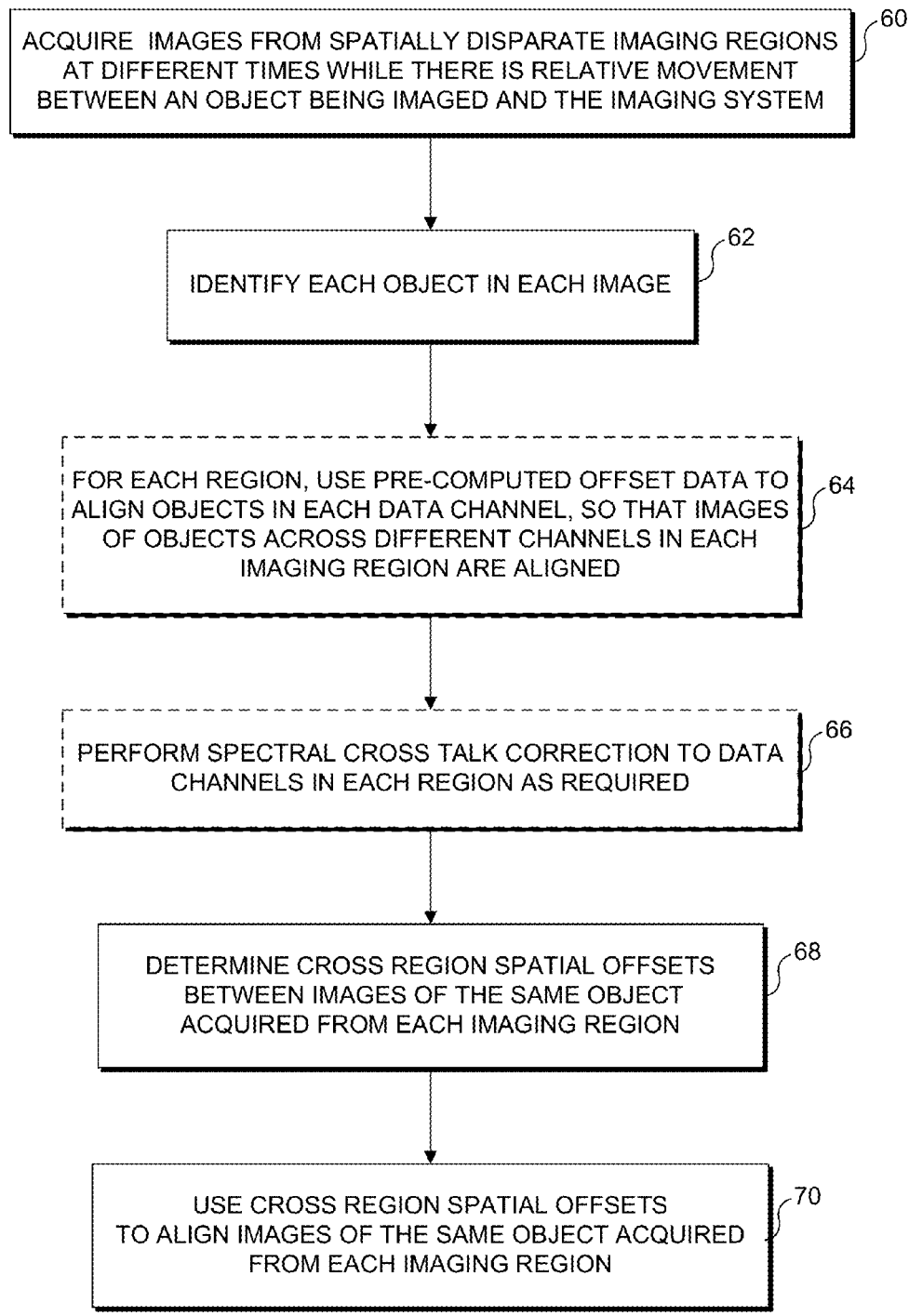
Figure 11:
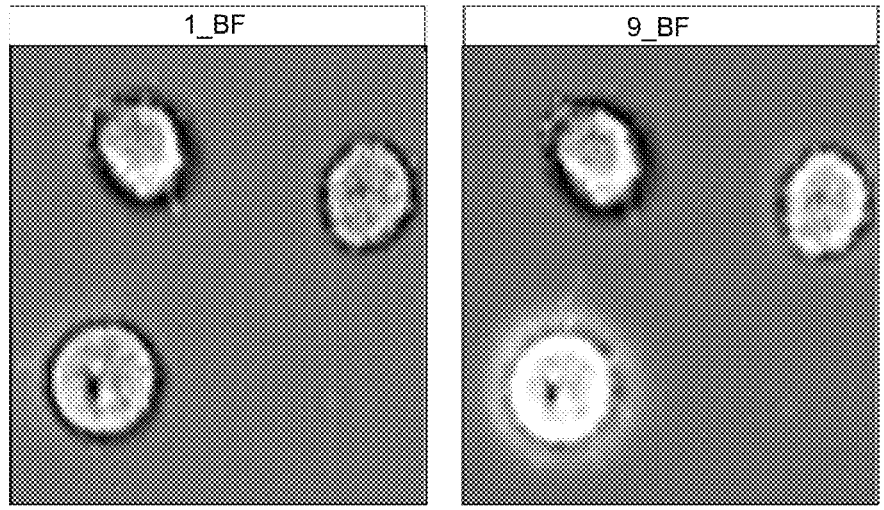
Figure 12:
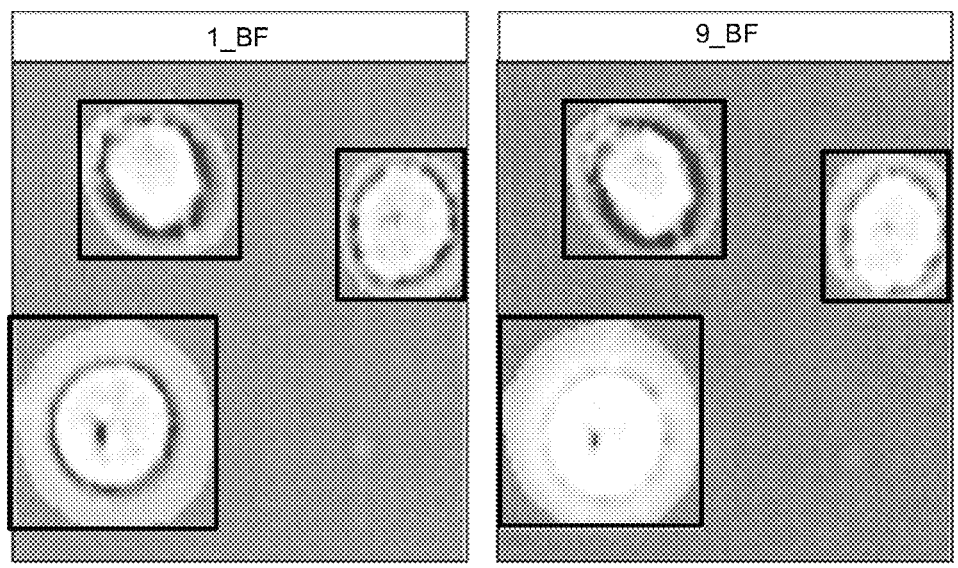
Figure 14:
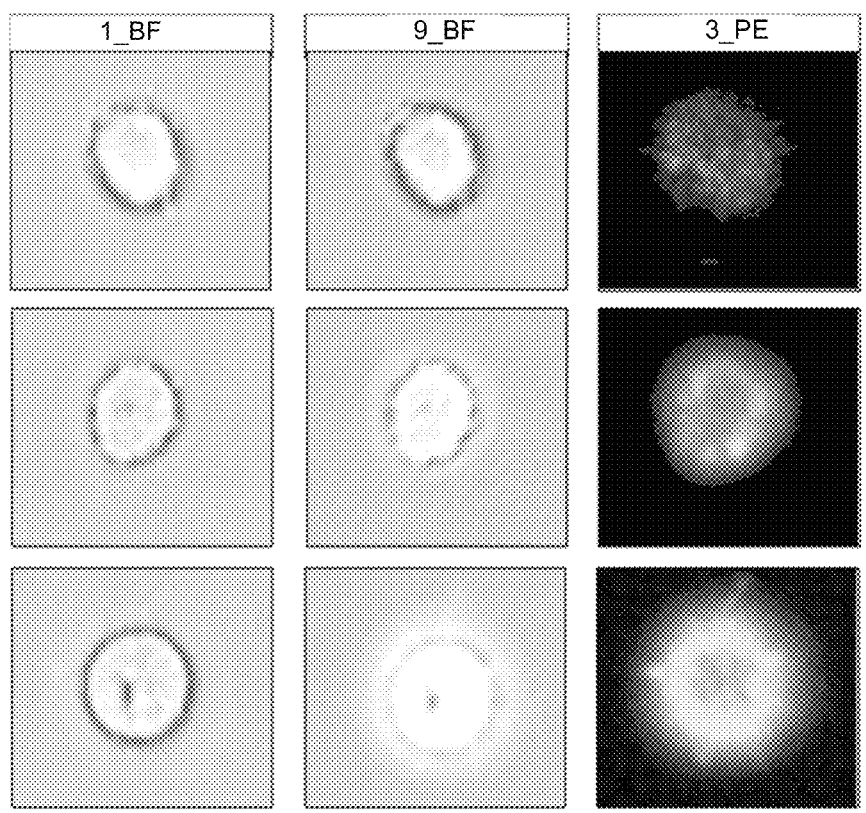

FIG. 3 (PRIOR ART) is a flow chart showing the logical steps generally implemented in the crosstalk correction technique disclosed in U.S. Pat. No. 7,079,708 for correcting static spatial offsets and spectral crosstalk among a plurality of channels in a multi-channel imaging detector;

FIG. 4 (PRIOR ART) is a schematic diagram depicting three data images and one reference image of objects in a flow stream, showing the objects as misaligned (i.e., an example of static spatial offsets in the different channels of a multi-channel imaging detector);

FIG. 5A (PRIOR ART) is a schematic diagram of an exemplary flow imaging system for acquiring images from a single imaging region, which can be used to simultaneously collect a plurality of images from an object in flow from the single imaging region;

FIG. 5B (PRIOR ART) is a plan view of an exemplary flow imaging system that employs a spectral dispersion component comprising a plurality of stacked dichroic filters employed to spectrally separate the light to simultaneously collect a plurality of images from an object in flow from a single imaging region;

FIG. 5C (PRIOR ART) illustrates an exemplary set of images projected onto the TDI detector when using the spectral dispersing filter system of FIG. 5B;

FIG. 6 is a schematic diagram of a first embodiment of an exemplary flow imaging system for acquiring images from two different imaging regions that are spaced apart along an axis of motion, which can be used to simultaneously collect a plurality of images from an object in flow from the two different spaced apart imaging regions;

FIG. 7 is a side view of the flow imaging system of FIG. 6;

FIG. 8 is a side view (with exaggerated dimensions) of a second embodiment of an exemplary flow imaging system for acquiring images from two different imaging regions that are spaced apart along an axis of motion, which can be used to simultaneously collect a plurality of images from an object in flow from the two different spaced apart imaging regions using a single detector having a relatively large field of view;

FIG. 9 is a schematic diagram of a third embodiment of an exemplary flow imaging system for acquiring images from two different imaging regions that are spaced apart along an axis of motion, which can be used to simultaneously collect a plurality of images from an object in flow from the two different spaced apart imaging regions using a single detector, where optical components are used to direct light from the first and second imaging regions to the same detector;

FIG. 10 is a flow chart of an exemplary technique for correcting dynamic cross region spatial offsets from images collected using an imaging system that acquires images from two different imaging regions that are spaced apart along an axis of motion;

FIG. 11 includes two different images of the same three objects, each different image being acquired at one of two imaging regions spaced apart along an axis of motion between the objects and the imaging system used to acquire the two images;

FIG. 12 graphically illustrates a technique for identifying each object in the two images of FIG. 11 by using bounding rectangles;

FIG. 13A graphically illustrates a first table for correcting static spatial offsets in an exemplary imaging system based on FIG. 6, where a six channel imaging detector is used to acquire image data from each of two spaced apart imaging regions;

FIG. 13B graphically illustrates a second table for correcting spectral crosstalk in an exemplary imaging system based on FIG. 6, where a six channel imaging detector is used to acquire image data from each of two spaced apart imaging regions;

FIG. 14 includes three different types of images acquired using the exemplary imaging system based on FIG. 6, including brightfield images acquired from a first imaging region, brightfield images acquired from the second imaging region, and fluorescent images acquired from the first imaging region, and where the images in each row are of the same object, where the spectral crosstalk correction related to FIG. 13B having not yet been performed.

Figure 15:
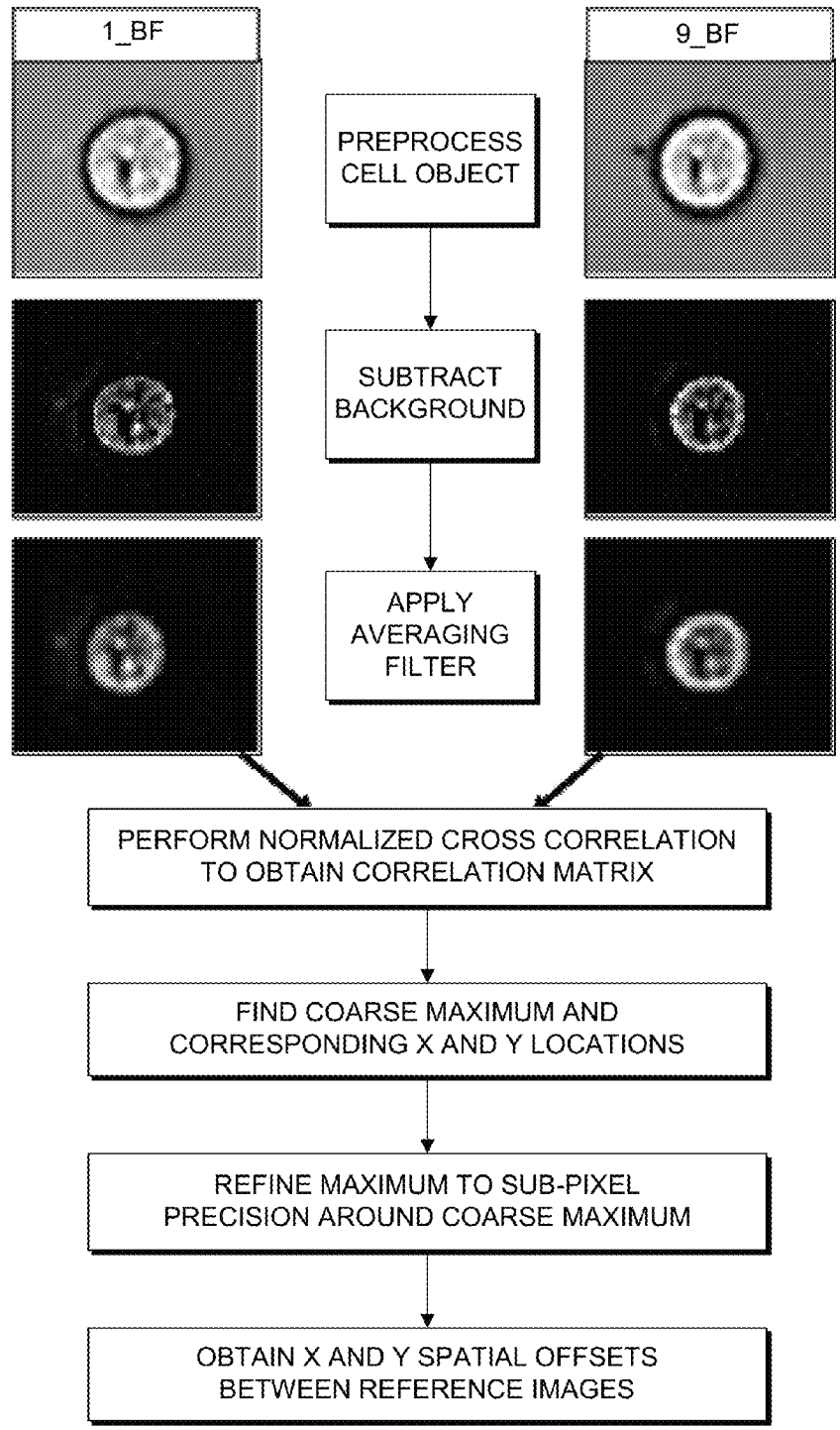
Figure 16A:
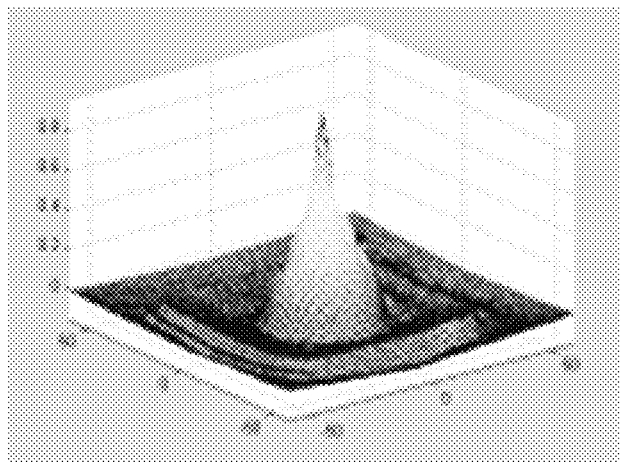
Figure 16B:
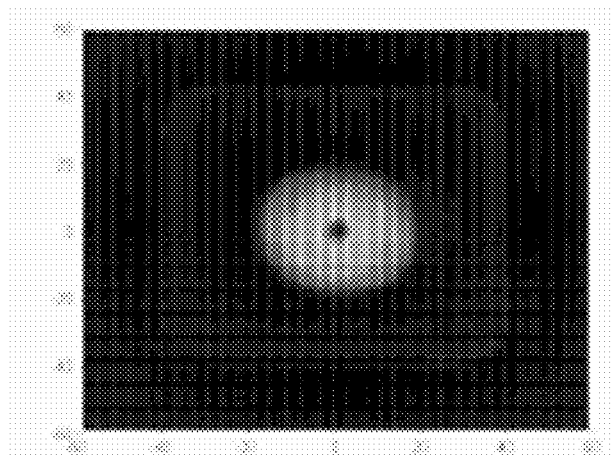
Figure 16C:
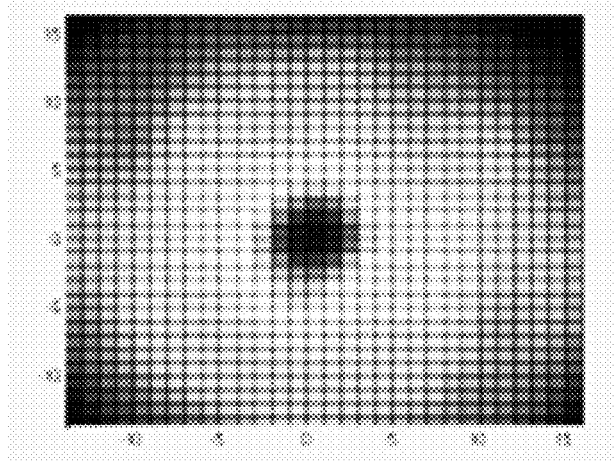
Figure 17:
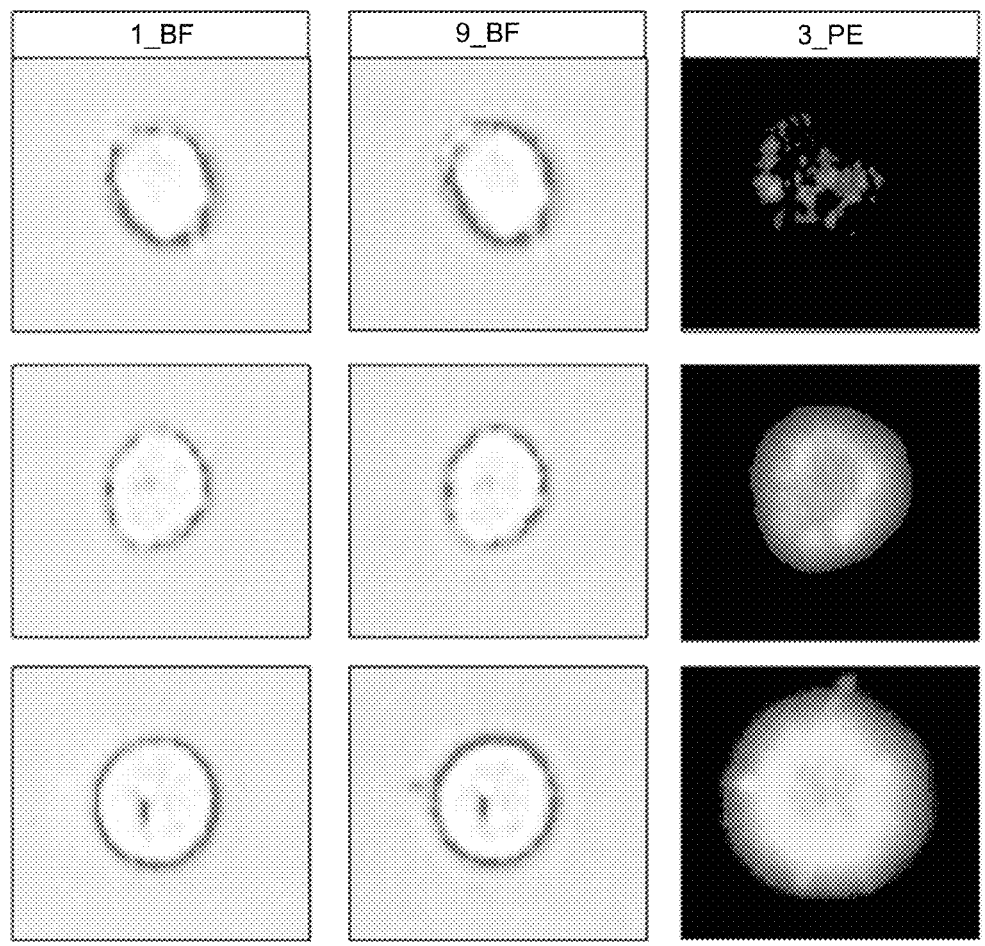
Figure 19:
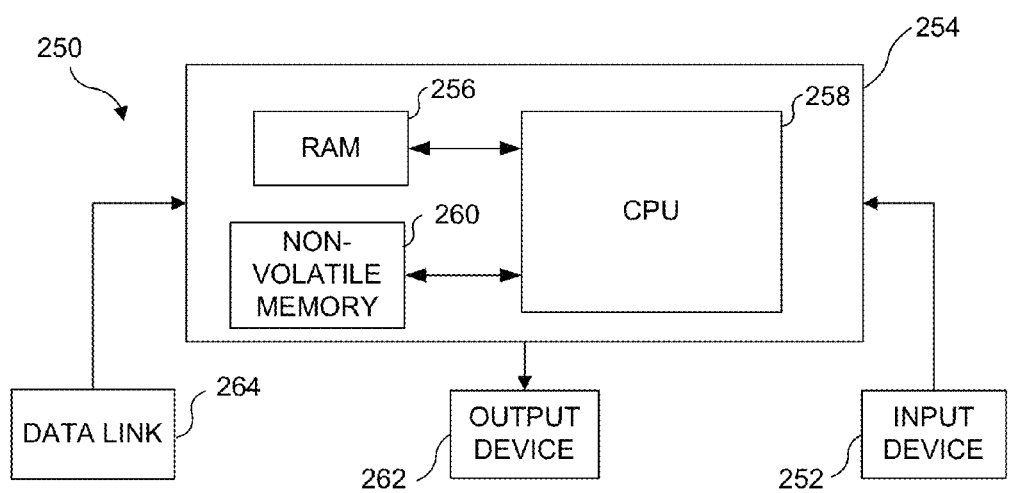
Figure 18:
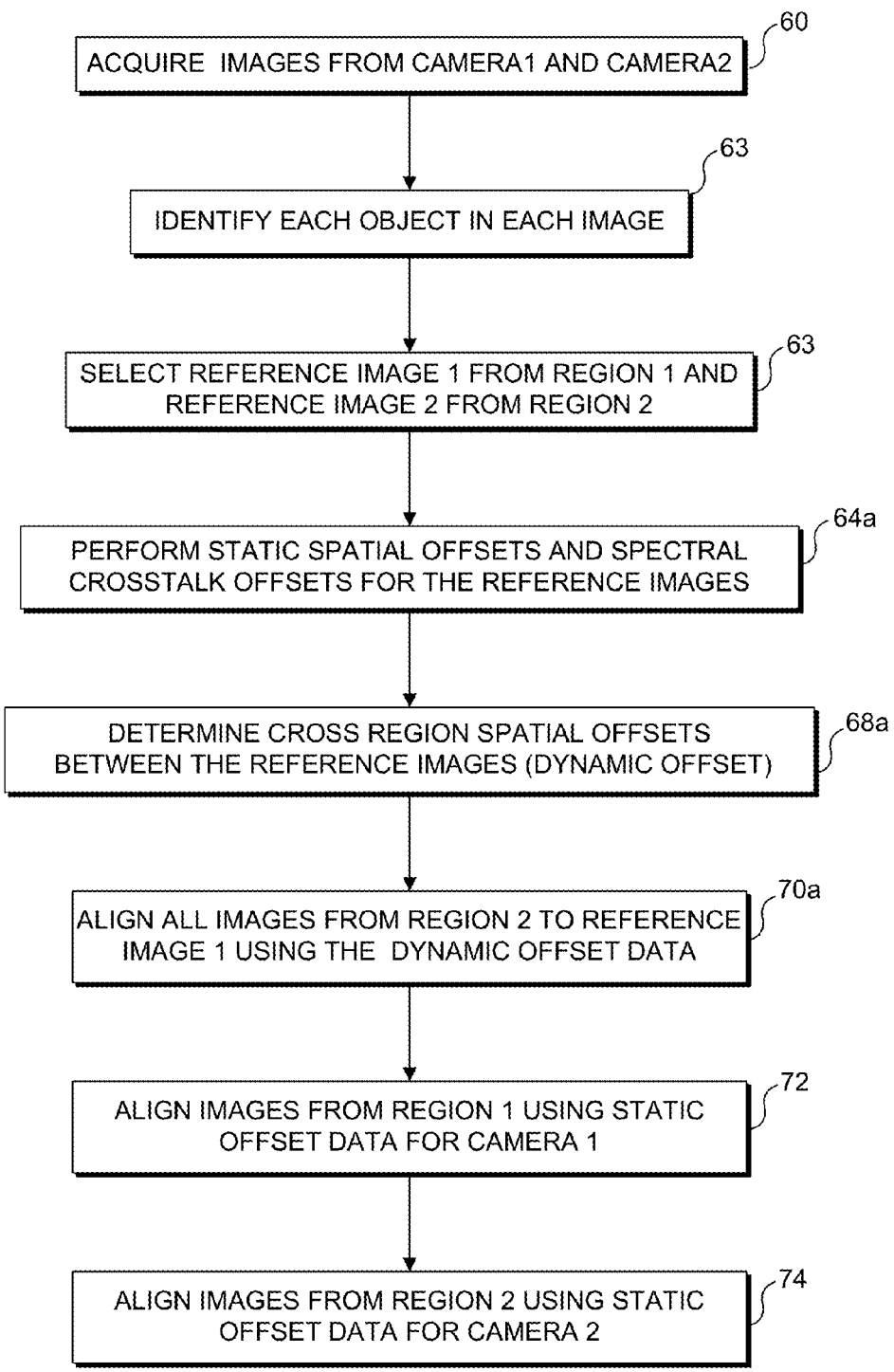
Figure 20:
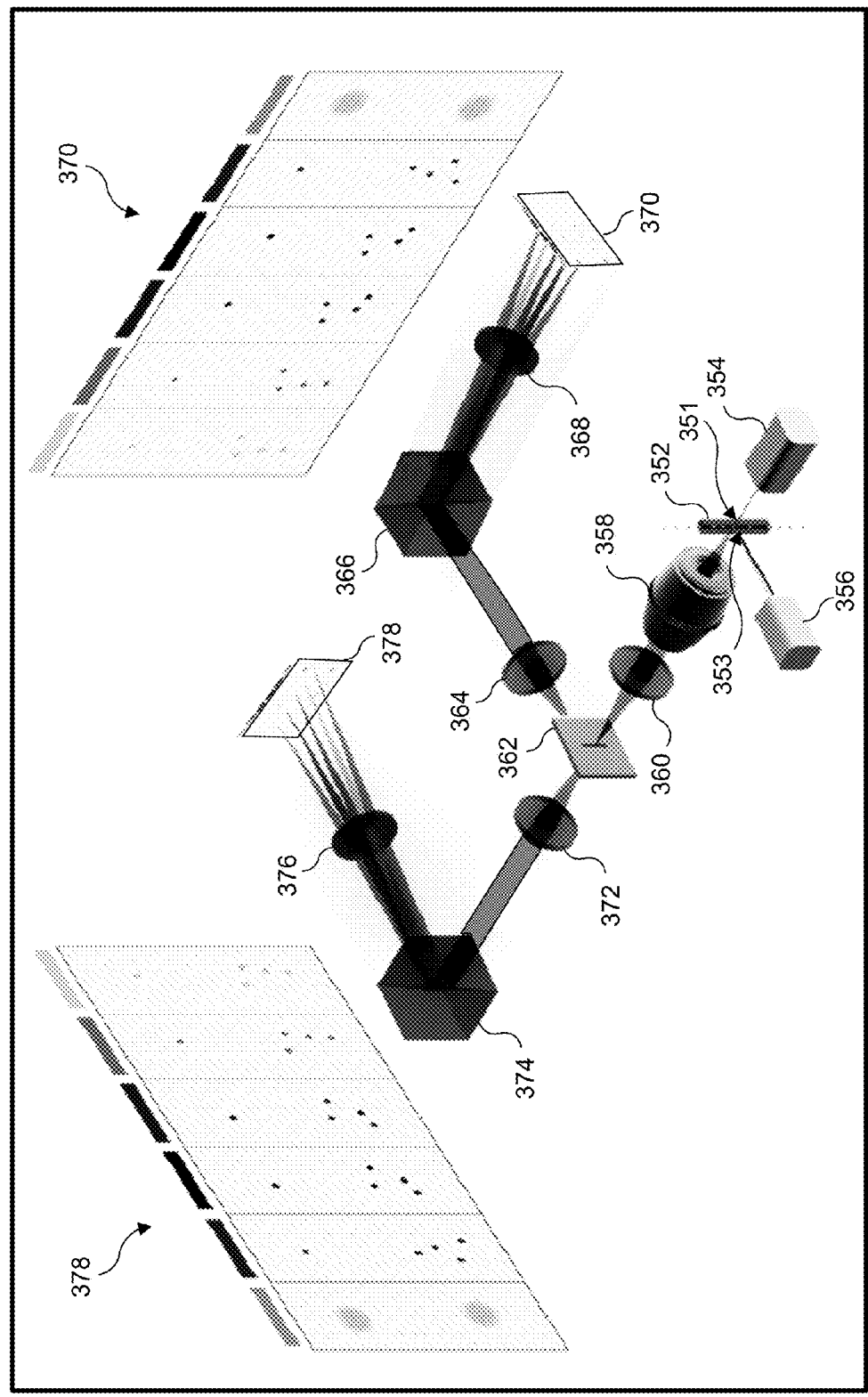

FIG. 15 is a flowchart illustrating an exemplary method for correcting dynamic cross region spatial offsets in the exemplary imaging system based on FIG. 6, representing a modified version of the method of FIG. 10;

FIG. 16A graphically illustrates a normalized cross-correlation surface plot, where the X and Y axis on the plot are pixel shifts, and the Z axis is the corresponding normalized cross-correlation value;

FIG. 16B graphically illustrates the normalized cross-correlation surface plot of FIG. 16A as seen from above;

FIG. 16C graphically illustrates a zoomed in view of the normalized cross-correlation surface plot of FIG. 16A, to show the highest value location;

FIG. 17 shows the images of FIG. 14 after dynamic cross region spatial offsets have been corrected using the method of FIG. 15;

FIG. 18 is a flowchart illustrating another exemplary sequence for correcting dynamic cross region spatial offsets;

FIG. 19 is a functional block diagram of an exemplary computing device for implementing the methods of FIGS. 10, 15 and 18; and FIG. 20 is a schematic diagram of an exemplary flow imaging system for acquiring images from two different imaging regions that are spaced apart along an axis of motion, which can be used to simultaneously collect a plurality of images from an object in flow from the two different spaced apart imaging regions, where a common objective is used to acquire light from a field of view that encompasses both imaging regions.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein. Further, it should be understood that any feature of one embodiment disclosed herein can be combined with one or more features of any other embodiment that is disclosed, unless otherwise indicated.

The concepts disclosed herein were developed to provide greater accuracy to multi-channel imaging systems developed by applicants, where up to twelve images of an object, such as a cell, are acquired. Such data can be acquired using two different six channel detectors spaced apart along an axis of relative motion between the object and the detectors, or by using a single six channel detector having a sufficiently large field of view that six channels of data can be acquired from two spatially distinct locations along the axis of relative motion between the object and the detector (noting that the specific number of data channels is not limiting, and only a single channel of data need be acquired from each of two different locations spaced apart along an axis of motion between the object being imaged and the imaging system). In developing this technology, based on acquiring image data from different locations spaced apart along an axis of motion, applicants identified a type of spatial misalignment that could not be corrected using techniques previously developed by applicants (see U.S. Pat. No. 7,079,708, noted above) for image data acquired from only a single location (as opposed to two spaced apart locations). In U.S. Pat. No. 7,079,708, the spatial misalignment being corrected was a function of the instrument and optical components being used to acquire the image data (for example, beam splitters or mirrors were used to disperse light from the object to the plurality of different detector channels, and physical misalignment of such beam splitters or mirrors would result in spatial misalignment of images in the different data channels, which could be corrected using the techniques disclosed in that patent). In an imaging system where image data is acquired from different locations spaced apart on the axis of motion, applicants discovered that any error in the estimated speed of the object would result in an additional spatial misalignment error between images acquired at the first imaging location and images acquired at the second imaging location. The concepts disclosed herein are intended to correct this newly identified source of spatial misalignment, which at times is referred to as a dynamic spatial offset (in contrast to the spatial offsets described in U.S. Pat. No. 7,079,708, which are static unless changes are made to the optical components or detector in the imaging system to cause a change in the spatial offsets induced by the instrumentation).

Exemplary Prior Art Image Alignment Techniques

Before discussing the newly developed concepts, it will be helpful to briefly discuss the imaging system and spatial alignment techniques disclosed in U.S. Pat. No. 7,079,708. Note the techniques disclosed in U.S. Pat. No. 7,079,708 were developed (in part) to spatially align a plurality of images acquired from the same location, either using a plurality of detectors all collecting light from the object at the same time, or using a single multi-channel detector and an optical system to disperse light from the object to different channels on the multi-channel detector.

Figures 1A, 1B:
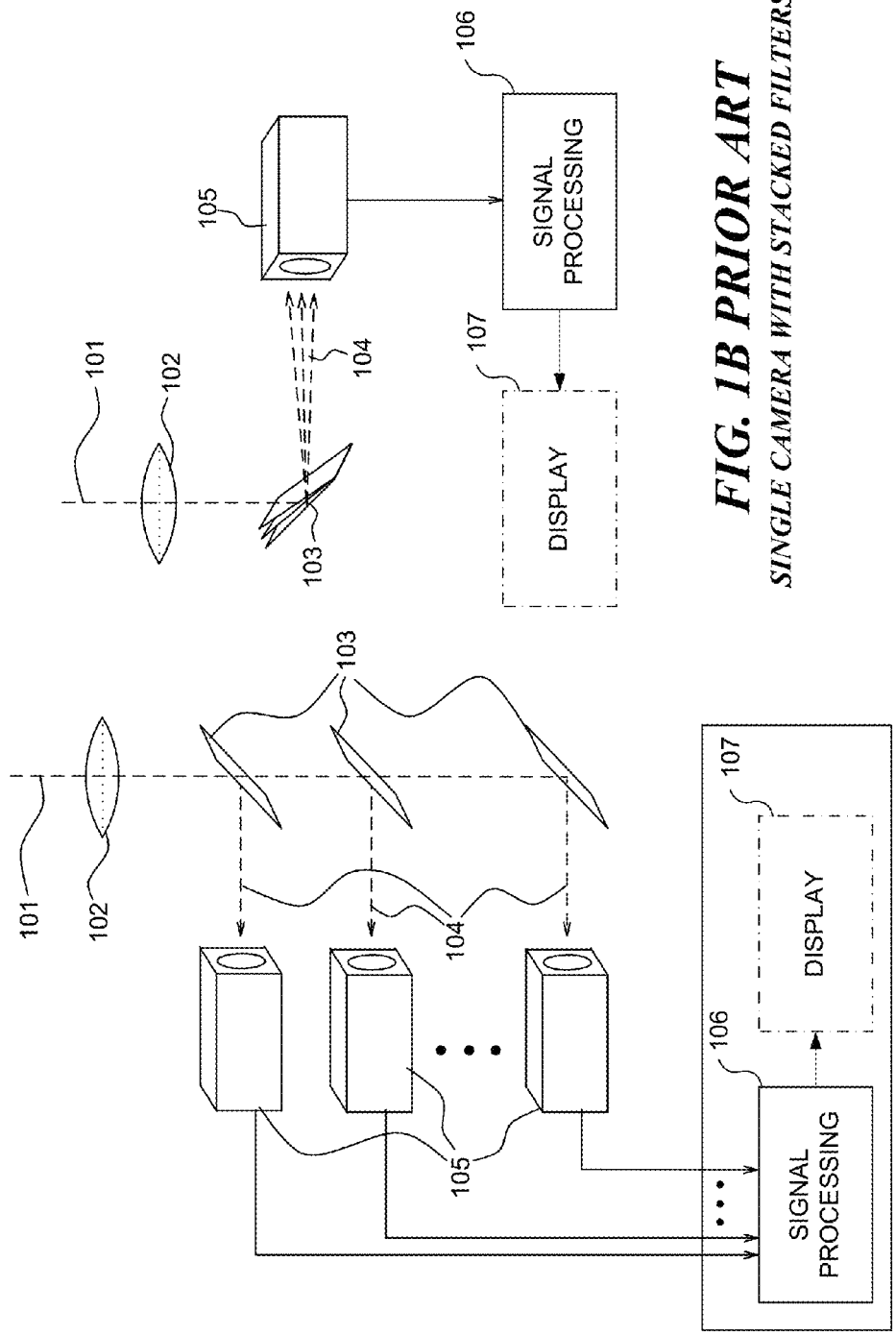
FIG. 1A (PRIOR ART) is a schematic diagram of an image collection and capture system of a multi-channel optical imaging instrument that includes a plurality of cameras, with one camera and one filter per channel.
FIG. 1B (PRIOR ART) is a schematic diagram of an image collection and capture system for an optical imaging system accomplishing multi-parametric imaging with a single camera and a plurality of filters.

Prior Art FIGS. 1A and 1B illustrate two configurations of an instrument for simultaneously acquiring a plurality of images of an object (either of which could be used at one of, or both of, the spaced apart imaging locations disclosed herein). FIG. 1A shows an embodiment that utilizes a plurality of photosensitive cameras 105. Lens 102 is used to form images on the photosensitive detector arrays of cameras 105. The light along each image formation path 101 is filtered by specially designed mirrors 103 that transmit light in a first range of wavelengths and reflect light in a second range of wavelengths, defining a plurality of different wavebands 104 that are received by individual cameras 105. The signals from cameras 105 are processed by signal processing means 106, which aligns the signals relative to each other, and reduces crosstalk between signals. An optional element is a display 107, on which the plurality of images corresponding to the processed signals can be displayed to a user.

An alternative configuration for an imaging system usable to simultaneously acquire a plurality of images of an object is shown in FIG. 1B. In this configuration, a single camera 105 is used to form an image in which light from a plurality of sources is filtered and reflected by a set of mirrors 103. Each mirror reflects light in a different waveband, forming a plurality of images in corresponding different regions of the camera's photosensitive array. The light reflected by the first mirror is incident on a first region, while the light transmitted by the first mirror in the stack falls on the face of the second mirror, which reflects light onto a second region of the camera's photosensitive detector. The successive reflection and transmission by the mirror stack produces a plurality of spectrally separated images, and single camera 105 produces a multi-channel signal corresponding to those images formed on each region of the camera's photosensitive detector. These different signals are processed by signal processing means 106 and optionally displayed on display 107.

It should be understood, in the context of discussing an imaging system configured to acquire image data from two different imaging regions spaced apart along an axis of motion between the imaging system and the object, that multi-channel data can be acquired from each imaging region using either a plurality of imaging detectors per imaging region (the technique used in FIG. 1A) or using a single multi-channel imaging detector (the technique used in FIG. 1B). Indeed, one of the two spaced apart imaging regions could use a plurality of individual imaging detectors to acquire image data from that imaging region (the technique used in FIG. 1A), while the other of the two spaced apart imaging regions could use a single multi-channel imaging detector (the technique used in FIG. 1B) to acquire the image data from that imaging region. Thus, in addition to providing background information to facilitate understanding the dynamic spatial offset techniques disclosed herein, FIGS. 1A and 1B provide different imaging detector configurations that can be used with the techniques disclosed herein to acquire and spatially align image data acquired from two imaging regions spaced apart along an axis of motion between the object being imaged and the imaging system.

Figure 2:
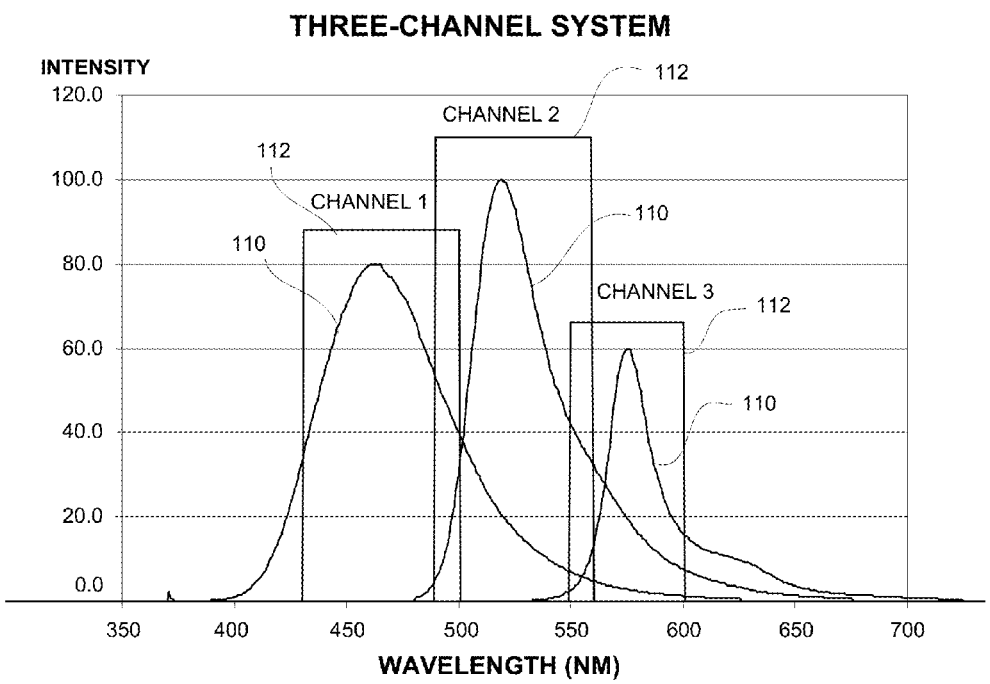
FIG. 2 (PRIOR ART) is a graph of wavelength vs. intensity for three optical signal spectra and idealized passbands of corresponding bandpass filters.

Returning to the background information related to U.S. Pat. No. 7,079,708, ideally, the light being imaged by the imaging systems of FIGS. 1A and 1B comprises wavelengths entirely encompassed within the passbands of the various channels. In that case, each color of light, such as red, contributes to only one image (e.g., an image of an object that is the source of the color of light in that channel). In many practical applications, however, the light that forms images in each channel spans a range of wavelengths broader than the passband of an associated filter for the channel, as shown in FIG. 2. In this example, light 110 from each source is received in three channels 112. The signal conveyed in each channel is then a composite of information for the multiple sources. The object of the spectral crosstalk and spatial alignment techniques disclosed in U.S. Pat. No. 7,079,708 is to process the signals from the plurality of channels to deliver the information for each source when displaying the image for that source.

FIG. 3 illustrates the core processes carried out in the spectral crosstalk and spatial alignment techniques disclosed in U.S. Pat. No. 7,079,708. Image data is processed to implement both a first spatial correction and a second spectral correction. It should be noted that FIG. 3 illustrates the data flow used in the technique, as opposed to a graphical depiction of a sequence of logical steps. The stage of calibrating for spatial correction parameters is represented by a block 301. In block 301, a calibration image is obtained from actual biological specimens, or artificial specimens (e.g., flow beads). U.S. Pat. No. 7,079,708 disclosed that spatial offsets could be determined in real time, or from calibration images acquired before data correlating to actual samples are generated. Empirical studies indicated that such pre-computed offsets were relatively static, and pre-computed offset data could be used with good results (hence the use of the term static spatial offsets to refer to such instrument specific offsets). The spatial correction parameters are determined in a block 302. Once the spatial correction parameters are computed, the spectral correction parameters are generated in a block 303. Note that the spectral calibration process requires the use of a control, whereas any sample can be used to provide spatial correction data. The control is preferably a biological specimen or an artificial specimen to which a single known fluorophore has been attached. The fluorophore selected preferably has the characteristic of having a fluorescent signature primarily limited to a single one of the multi-channels. Some small amount of "spill over" from the single fluorophore will likely exist in the other channels. Based on the known spectral signature of the control, and the multi-channel data corresponding to that control, spectral corrections can be determined to eliminate such spill over, or crosstalk. Such a control is also referred to as a single source, because its spectral signature is substantially confined to a single channel. A control can be imaged alone, as part of a calibration phase that occurs before acquiring data from samples. In at least one embodiment, a control is introduced into a batch of samples, so that the calibration can occur during the processing of a batch of samples.

Once the spatial and spectral correction factors have been determined, the signal processing can be performed on the ensemble of images. In a block 304, the ensemble of images are input. The spatial corrections (determined in block 302) are applied to the ensemble of images in a block 305. Next, the spectral crosstalk corrections determined in block 303 are applied to the spatially corrected ensemble of images in a block 306. It is important that the spatial corrections be applied before the spectral corrections are applied. The spatially and spectrally corrected ensemble of images is available as data output at a block 307.

FIG. 4 depicts a four-channel system with a reference channel 1001. The other three channels 1002, 1003, and 1004 are data channels. Preferably, reference channel 1001 corresponds to a brightfield image, while channels 1002-1004 correspond to fluoresced images. As shown in the Figure, the images from the data channels are spatially misaligned vertically (i.e., in time) with the corresponding images from the reference channel. The techniques disclosed in U.S. Pat. No. 7,079,708 enable the images in different data channels to be spatially aligned. Once the images are aligned, the spectral crosstalk noted in connection with FIG. 2 can be corrected.

Exemplary Prior Art Systems Acquiring Image Data from One Location Along Axis

As discussed above, the spatial alignment techniques disclosed herein are needed when image data is acquired from two different locations spaced apart along an axis of motion between an object and imaging components used to acquire the image data. As the current spatial alignment technique was developed when modifying applicants' earlier technology (used to acquire image data from only a single location along an axis of motion between an object and the imaging component), it may be useful to briefly discuss imaging systems that can be used to acquire image data from one such location (noting that one or more of the elements in these prior art systems can be incorporated into the new imaging systems disclosed herein, which acquire image data from two spaced apart locations).

FIG. 5A is a schematic diagram of a flow imaging system 510 that uses TDI when capturing images of objects 502 (such as biological cells), entrained in a fluid flow 504. System 510 includes a velocity detecting subsystem that is used to synchronize a TDI imaging detector 508 with the flow of fluid through the system. Significantly, imaging system 510 is capable of simultaneously collecting a plurality of images of an object. A particularly preferred implementation of imaging system 510 is configured for multi-spectral imaging and can operate with six spectral channels: DAPI fluorescence (400-460 nm), Dark field (460-500 nm), FITC fluorescence (500-560 nm), PE fluorescence (560-595 nm), Brightfield (595-650 nm), and Deep Red (650-700 nm). The TDI detector can provide 10 bit digital resolution per pixel. The numeric aperture of the preferred imaging system is typically 0.75, with a pixel size of approximately 0.5 microns. However, those skilled in the art will recognize that this flow imaging system is neither limited to six spectral channels, nor limited to either the stated aperture size or pixel size and resolution.

Moving objects 502 are illuminated using a light source 506. The light source may be a laser, a light emitting diode, a filament lamp, a gas discharge arc lamp, or other suitable light emitting source, and the system may include optical conditioning elements such as lenses, apertures, and filters that are employed to deliver broadband or one or more desired wavelengths or wavebands of light to the object with an intensity required for detection of the velocity and one or more other characteristics of the object. Light from the object is split into two light paths by a beam splitter 503. Light traveling along one of the light paths is directed to the velocity detector subsystem, and light traveling along the other light path is directed to TDI imaging detector 508. A plurality of lenses 507 are used to direct light along the paths in a desired direction, and to focus the light. Although not shown, a filter or a set of filters can be included to deliver to the velocity detection subsystem and/or TDI imaging detector 508, only a narrow band of wavelengths of the light corresponding to, for example, the wavelengths emitted by fluorescent or phosphorescent molecules in/on the object, or light having the wavelength(s) provided by the light source 506, so that light from undesired sources is substantially eliminated.

The velocity detector subsystem includes an optical grating 505a that amplitude modulates light from the object, a light sensitive detector 505b (such as a photomultiplier tube or a solid-state photodetector), a signal conditioning unit 505c, a velocity computation unit 505d, and a timing control unit 505e, which assures that TDI imaging detector 508 is synchronized to the flow of fluid 504 through the system. The optical grating preferably comprises a plurality of alternating transparent and opaque bars that modulate the light received from the object, producing modulated light having a frequency of modulation that corresponds to the velocity of the object from which the light was received. Preferably, the optical magnification and the ruling pitch of the optical grating are chosen such that the widths of the bars are approximately the size of the objects being illuminated. Thus, the light collected from cells or other objects is alternately blocked and transmitted through the ruling of the optical grating as the object traverses the interrogation region, i.e., the field of view. The modulated light is directed toward a light sensitive detector, producing a signal that can be analyzed by a processor to determine the velocity of the object. The velocity measurement subsystem is used to provide timing signals to TDI imaging detector 508.

Beam splitter 503 has been employed to divert a portion of light from an object 502 to light sensitive detector 505b, and a portion of light from object 502a to TDI imaging detector 508. In the light path directed toward TDI imaging detector 508, there is a plurality of stacked dichroic filters 509, which separate light from object 502a into a plurality of wavelengths. One of lenses 507 is used to form an image of object 502a on TDI imaging detector 508.

The theory of operation of a TDI detector like that employed in system 510 is as follows. As objects travel through a flow tube 511 (FIG. 5A) and pass through the volume imaged by the TDI detector, light from the objects forms images of the objects, and these images travel across the face of the TDI detector. The TDI detector preferably comprises a charge coupled device (CCD) array, which is specially designed to allow charge to be transferred on each clock cycle, in a row-by-row format, so that a given line of charge remains locked to, or synchronized with, a line in the image. The row of charge is clocked out of the array and into a memory when it reaches the bottom of the array. The intensity of each line of the signal produced by the TDI detector corresponding to an image of an object is integrated over time as the image and corresponding resulting signal propagate over the CCD array. This technique greatly improves the signal-to-noise ratio of the TDI detector compared to non-integrating type detectors—a feature of great benefit in a detector intended to respond to images from low-level fluorescence emission of an object. Proper operation of the TDI detector requires that the charge signal be clocked across the CCD array in synchronization with the rate at which the image of the object moves across the CCD array. An accurate clock signal to facilitate this synchronization can be provided by determining the velocity of the object, and the concepts disclosed herein use an accurate estimate of the object's velocity, and thus, of the velocity of the image as it moves over the CCD array of the TDI detector. A flow imaging system of this type is disclosed in commonly assigned U.S. Pat. No. 6,249,341, the complete disclosure, specification, and drawings of which are hereby specifically incorporated herein by reference.

Additional exemplary flow imaging systems are disclosed in commonly assigned U.S. Pat. No. 6,211,955 and U.S. Pat. No. 6,608,682, the complete disclosure, specification, and drawings of which are hereby specifically incorporated herein by reference as background material. The imaging systems described above and in these two patents in detail, and incorporated herein by reference, have substantial advantages over more conventional systems employed for the acquisition of images of biological cell populations. These advantages arise from the use in several of the imaging systems of an optical dispersion system, in combination with a TDI detector that produces an output signal in response to the images of cells and other objects that are directed onto the TDI detector. Significantly, multiple images of a single object can be collected at one time. The image of each object can be spectrally decomposed to discriminate object features by absorption, scatter, reflection, or emissions, using a common TDI detector for the analysis. Other systems include a plurality of detectors, each dedicated to a single spectral channel.

The imaging system of FIG. 5B employs a spectral dispersion filter assembly that does not convolve the acquired images with the emission spectra of the light forming the images, thereby eliminating the need for deconvolution of the emission spectra from the image. This system uses a non-distorting spectral dispersion system 150 that employs a five color stacked wedge spectral dispersing filter assembly 154.

In FIG. 5B (which is a plan view), a fluid flow 122 entrains an object 124 (such as a cell, but alternatively, a small particle) and carries the object through the imaging system. The direction of the fluid flow in FIG. 5B is into (or out of) the drawing sheet. Light 130 from object 124 passes through collection lenses 132a and 132b that collect the light, producing collected light 134, which is approximately focused at infinity, i.e. the rays of collected light from collection lens 132b are generally parallel. Collected light 134 enters spectral dispersing filter assembly 154, which disperses the light, producing dispersed light 135. The dispersed light then enters imaging lenses 140a and 140b, which focuses dispersed light 135 onto a TDI detector 144.

The spectral dispersing filter assembly splits the light into a plurality of light beams having different bandwidths. Each light beam thus produced is directed at a different nominal angle so as to fall upon a different region of TDI detector 144. The nominal angular separation between each bandwidth produced by the spectral dispersing filter assembly 154 exceeds the field angle of the imaging system in object space thereby preventing overlap of the field images of various bandwidths on the detector.

Spectral dispersing filter assembly 154 comprises a plurality of stacked dichroic wedge filters, including a red dichroic filter R, an orange dichroic filter O, a yellow dichroic filter Y, a green dichroic filter G, and a blue dichroic filter B. Red dichroic filter R is placed in the path of collected light 134, oriented at an angle of approximately 44.0° relative to an optic axis 152 of collection lenses 132a and 132b. Light of red wavelengths and above, i.e., >640 nm, is reflected from the surface of red dichroic filter R at a nominal angle of 1°, measured counter-clockwise from a vertical optic axis 156. The light reflected by red dichroic filter R leaves spectral dispersing filter assembly 154 and passes through imaging lenses 140a and 140b, which cause the light to be imaged onto a red light receiving region of TDI detector 144, which is disposed toward the right end of the TDI detector, as shown in FIG. 5B.

Orange dichroic filter O is disposed a short distance behind red dichroic filter R and is oriented at an angle of 44.5 degrees with respect to optic axis 152. Light of orange wavelengths and greater, i.e., >610 nm, is reflected by orange dichroic filter O at a nominal angle of 0.5° with respect to vertical optic axis 156. Because the portion of collected light 134 comprising wavelengths longer than 640 nm was already reflected by red dichroic filter R, the light reflected from the surface of orange dichroic filter O is effectively bandpassed in the orange colored region between 610 nm and 640 nm. This light travels at a nominal angle of 0.5° from vertical optic axis 156, and is imaged by imaging lenses 140a and 140b so as to fall onto an orange light receiving region disposed toward the right hand side of TDI detector 144 between a center region of the TDI detector and the red light receiving region, again as shown in FIG. 5B.

Yellow dichroic filter Y is disposed a short distance behind orange dichroic filter O and is oriented at an angle of 45° with respect to optic axis 152. Light of yellow wavelengths, i.e., 560 nm and longer, is reflected from yellow dichroic filter Y at a nominal angle of 0.0° with respect to vertical optic axis 156. Wavelengths of light reflected by yellow dichroic filter Y are effectively bandpassed in the yellow region between 560 nm and 610 nm and are imaged by imaging lenses 140a and 140b near vertical optic axis 156 so as to fall on a yellow light receiving region toward the center of TDI detector 144.

In a manner similar to dichroic filters R, O, and Y, dichroic filters G and B are configured and oriented so as to image green and blue light wavebands onto respective green and blue light receiving regions of TDI detector 144, which are disposed toward the left-hand side of the TDI detector. By stacking the dichroic filters at different predefined angles, spectral dispersing filter assembly 154 collectively works to focus light within predefined wavebands of the light spectrum onto predefined regions of TDI detector 144.

The wedge shape of the dichroic filters in the preceding discussion allows the filters to be placed in near contact, in contact or possibly cemented together to form the spectral dispersing filter assembly 154. The angle of the wedge shape fabricated into the substrate for the dichroic filter allows easy assembly of the spectral dispersing filter assembly 154, forming a monolithic structure in which the wedge-shaped substrate is sandwiched between adjacent dichroic filters. If the filters are in contact with each other or cemented together, the composition of the materials that determine the spectral performance of the filter may be different from those which are not in contact. Those of ordinary skill in the art will appreciate that flat, non wedge-shaped substrates could be used to fabricate the spectral dispersing filter assembly 154. In this case another means such as mechanically mounting the filters could be used to maintain the angular relationships between the filters.

In addition to the foregoing configuration, non-distorting spectral dispersion system 150 may optionally include a detector filter assembly 158 to further attenuate undesired signals in each of the light beams, depending upon the amount of rejection required for out-of-band signals. In the embodiment shown in FIG. 5B, light may pass through each dichroic filter in the spectral dispersing filter assembly 154 twice before exiting the spectral dispersing filter assembly 154. This condition will further attenuate out-of-band signals, but will also attenuate in-band signals.

The foregoing description illustrates the use of a five color system. Those skilled in the art will appreciate that a spectral dispersing component with more or fewer filters may be used in these configurations in order to construct a system covering a wider or a narrower spectral region, or different passbands within a given spectral region. Likewise, those skilled in the art will appreciate that the spectral resolution of the present invention may be increased or decreased by appropriately choosing the number and spectral characteristics of the dichroic and/or bandpass filters that are used. Furthermore, those skilled in the art will appreciate that the angles or orientation of the filters may be adjusted to direct light of a given bandwidth onto any desired point on the TDI detector. In addition, there is no need to focus the light in increasing or decreasing order by wavelength. For example, in fluorescence imaging applications, one may wish to create more spatial separation on the TDI detector between the excitation and emission wavelengths by changing the angles at which the filters corresponding to those wavelengths are oriented with respect to the optic axes of the system. Finally, it will be clear to those skilled in the art that dispersion of the collected light may be performed on the basis of non-spectral characteristics, including angle, position, polarization, phase, or other optical properties.

FIG. 5C illustrates the distribution of images on TDI detector 144 corresponding to imaging a plurality of cells 280-284 using non-distorting spectral dispersion system 150. Significantly, the field angle of system 150 is orthogonal to flow in object space, such that the individual images are laterally dispersed across detector 144 (as indicated on FIG. 5C), substantially orthogonal to a direction of a motion of the respective images across the TDI detector (i.e., the object moves vertically across the detector, and the plurality of images are dispersed horizontally across the detector).

In this particular configuration, the field angle in object space is less than +/−0.25°. Those skilled in the art will appreciate that the field angle can be made larger or smaller. To the extent that the field angle is made larger, for example, to image cells over a wider region on a slide or in a broad flat flow, the field angle at the detector will increase in proportion to the number of colors used. FIG. 5C illustrates the image projected onto the detector when three cells 280, 282 and 284 are flowing through the field of view. Light scatter images of cells 280, 282, and 284 are seen on the left hand side of the detector denoted as the BLUE area. Images of cell nuclei 202 stained with a green fluorescent dye are seen in the GREEN area of the detector. Three differently-colored genetic probes 204, 205, and 206 are also employed for the analysis of the sex chromosomes within the cells. Probe 204 stains the X chromosome with an orange fluorescing dye, probe 205 stains the Y chromosome with yellow fluorescing dye, and probe 206 stains the inactive X chromosome in female cells with a red fluorescing dye. Cell 282 is imaged onto the detector as shown in FIG. 5C. An image 286 of probe 204 from cell 282 is seen in the ORANGE area of the detector. Likewise an image 288 of probe 205 from cell 282 is seen in the YELLOW area of the detector. The signal on the detector is processed to determine the existence and position of these images on the detector to determine that cell 282 is a male cell. In a similar manner, cells 280 and 284 contain probes 204 and 206, which create images 290 and 292 in the ORANGE area of the detector, and images 294 and 296 in the RED area of the detector, indicating that these cells are female, respectively.

Newly Developed Imaging Systems that Acquire Images from Spaced Apart Locations

While the imaging systems discussed above are useful, most readily available imaging detectors are limited to six channels. To provide additional channels of image data, which would enable biological cells to be tagged with more complicated fluorescent tags (including additional individual fluorescent dyes or combinations of fluorescent dyes), applicants developed several different systems to provide such additional channels. Each newly developed imaging system collects image data from an object while there is relative motion between the object and the imaging detector(s) (noting that most often the object is in motion, but in various embodiments the object can be stationary while the detectors are moved) from two different locations spaced apart along the axis of movement. An analysis of the data from such systems indicated that the spatial and spectral correction technique of U.S. Pat. No. 7,079,708 was not able to correct the spatial offsets and spectral crosstalk in the new systems, leading to the development of the spatial correction techniques disclosed herein.

FIGS. 6-9 relate to imaging systems configured to enable image data to be collected from two different imaging regions spaced apart along an axis of motion between an object being imaged and the imaging system. These Figures include relative positions of basic optical components used to convey light from two different imaging regions spaced apart along an axis of motion, and one or more imaging detectors used to collect image data. These Figures do not include additional components, such as light sources, that may be used in connection with the imaging systems. In at least some embodiments (particularly embodiments where the objects being imaged are cells that may have been tagged with one or more fluorescent dyes), a light source (such as a laser, although other light sources can also be used) will be employed to illuminate each imaging region, to stimulate fluorescent emissions from fluorescent dyes used to tag the object being imaged (often a biological cell). The artisan of skill will recognize that such light sources can be readily incorporated into any of the imaging systems of FIGS. 6-9.

A first imaging system 20 is schematically illustrated in FIG. 6, in connection with producing images of moving objects such as cells that are conveyed by a fluid flow 22 through the imaging system. In FIG. 6, fluid flow 22 entrains an object (such as a cell, but alternatively, a small particle) and carries the object through the imaging system. The direction of the fluid flow in FIG. 6 is from top to bottom, as indicated by the arrow to the left of the Figure. Light 30a from a first imaging region 24a passes through a collection lens 32a, which produces collected light 34a (approximately focused at infinity, i.e., the rays of collected light from the collection lens are generally parallel). Collected light 34a enters a filter stack 36a such as discussed above in connection with FIG. 5B), which disperses the light, producing dispersed light 38a. The dispersed light then enters imaging lens 40a, which focuses light 42a onto a TDI detector 44a (thereby acquiring image data from the first imaging region).

System 20 includes an additional optical train to acquire image data from a second imaging region 24b, after the particle has moved away from imaging region 24a. Light 30b from second imaging region 24b passes through a collection lens 32b, which produces collected light 34b (approximately focused at infinity, i.e., the rays of collected light from the collection lens are generally parallel). Collected light 34b enters a filter stack 36b, which disperses the light, producing dispersed light 38b. The dispersed light then enters imaging lens 40b, which focuses light 42b onto a TDI detector 44b (thereby acquiring image data from the first imaging region).

To correlate image data acquired from first imaging region 24a with second imaging region 24b, one must know the velocity of the object being imaged. A velocity detection system, such as that discussed above in connection with FIG. 5A, can be employed to provide such a velocity estimate. Alternately, one could employ knowledge about the flow rate of the fluid in the flow imaging system (generally a user controllable parameter, as fluid flow is established using a fluid pump). The former technique is more accurate, while the latter technique, particularly when combined with the spatial offset correction techniques disclosed herein, also yields acceptable results. Imaging region 24a is spaced apart from imaging region 24b by a distance X along the axis of motion between the object being imaged and the image acquisition elements.

Note that the optical paths for each imaging region shown in FIG. 6 enables imaging of objects from two different directions, which can aid in distinguishing features that would otherwise overlap when viewed from a single direction. It should be understood that the configuration of the optical paths (enabling image data to be acquired from different directions for each imaging region, or the same direction) is not critical to the implementation of the dynamic spatial offset correction techniques disclosed herein, and that the concepts disclosed herein are not limited to any specific optical path configuration.

As will be evident in FIG. 7, which is a side view of system 20, each imaging region is large enough relative to the size of the object being imaged that the acquisition of image data from each imaging region can occur over time (as discussed above, the use of TDI imaging enables an improved signal to noise ratio to be achieved). FIG. 7 indicates that an object in imaging region 24a will be imaged at both a position 26a and a position 28a as it moves with fluid flow 22 (as well as the points between). As a consequence, images of each object moving through imaging region 24a will be produced on the detector at two discrete spatial positions 26a' and 28a', as indicated on the right side of FIG. 7. Alternatively, if FIG. 7 is depicting a single instant in time, positions 26a and 28a can represent the location of two separate objects, which are simultaneously imaged on the detector at positions 26a' and 28a'. Similarly, FIG. 7 indicates that an object in imaging region 24b will be imaged at both a position 26b and a position 28b as it moves with fluid flow 22 (as well as the points between). Images of each object moving through imaging region 24b will be produced on the detector at two discrete spatial positions 26b' and 28b', as indicated on the right side of FIG. 7.

In regard to imaging system 20 and all other imaging systems illustrated herein, it will be understood that the lenses and other optical elements illustrated are shown only in a relatively simple form. Thus, the collection lens is illustrated as a compound lens. Lens elements of different designs, either simpler or more complex, could be used in constructing the imaging system to provide the desired optical performance, as will be understood by those of ordinary skill in the art. The actual lenses or optical elements used in the imaging system will depend upon the particular type of imaging application for which the imaging system will be employed.

In each of the embodiments of the concepts disclosed herein, it will be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion but either in different directions or at different rates.

The TDI detector that is used in the various embodiments of the present invention preferably comprises a rectangular charge-coupled device (CCD) that employs a specialized pixel read out algorithm, as explained below. Non-TDI CCD arrays are commonly used for 2-dimensional imaging in cameras. In a standard CCD array, photons that are incident on a pixel produce charges that are trapped in the pixel. The photon charges from each pixel are read out of the detector array by shifting the charges from one pixel to the next, and then onto an output capacitor, producing a voltage proportional to the charge. Between pixel readings, the capacitor is discharged and the process is repeated for every pixel on the chip. During the readout, the array must be shielded from any light exposure to prevent charge generation in the pixels that have not yet been read.

In one type of TDI detector 44, which comprises a CCD array, the CCD array remains exposed to the light as the pixels are read out. The readout occurs one row at a time from the top toward the bottom of the array. Once a first row is read out, the remaining rows are shifted by one pixel in the direction of the row that has just been read. If the object being imaged onto the array moves in synchrony with the motion of the pixels, light from the object is integrated for the duration of the TDI detector's total readout period without image blurring. The signal strength produced by a TDI detector will increase linearly with the integration period, which is proportional to the number of TDI rows, but the noise will increase only as the square root of the integration period, resulting in an overall increase in the signal-to-noise ratio by the square root of the number of rows. One TDI detector suitable for use in the present invention is a Dalsa Corp., Type IL-E2 image sensor, although other equivalent or better image sensors can alternatively be used. The Dalsa image sensor has 96 stages or rows, each comprising 512 pixels; other types of image sensors useable in the present invention may have different configurations of rows and columns or a non-rectilinear arrangement of pixels. The Dalsa sensor has approximately 96 times the sensitivity and nearly 10 times the signal-to-noise ratio of a standard CCD array. The extended integration time associated with TDI detection also serves to average out temporal and spatial illumination variations, increasing measurement consistency.

In imaging system 20 and in other embodiments of the concepts disclosed herein that employ a fluid flow to carry objects through the imaging system, a flow-through cuvette or a jet (not shown) contains the cells or other objects being analyzed. The velocity and cellular concentration of the fluid may be controlled using syringe pumps, gas pressure, or other pumping methods (not shown) to drive a sample solution through the system to match the pixel readout rate of the TDI detector. However, it should be understood that the readout rate of the TDI detector can be selectively controlled, as required, to match the motion of the sample solution.

Various optical magnifications can be used to achieve a desired resolution of the object that is being imaged on the light sensitive regions (pixels) of the TDI detector. It is contemplated that in most embodiments, the optical magnification will fall within a range of 1:1 to 50:1, providing a substantial range in the number of light sensitive regions on the TDI detector on which images of the object are formed, also depending of course, on the actual size of the object being imaged and its distance from the imaging system. It is envisioned that the present invention can have applications ranging from the analysis of cells and other microscopic objects to the imaging of stellar objects.

It should be emphasized that the present invention is not limited to CCD types of TDI detectors. Other types of TDI detectors, such as complementary metal oxide semiconductor (CMOS) and multi-channel plate imaging devices might also be used for the TDI detector. It is important to understand that any pixelated device (i.e., having a multitude of light sensitive regions) in which a signal produced in response to radiation directed at the device can be caused to move through the device in a controlled fashion is suitable for use as the TDI detector in the present invention. Typically, the signal will move in synchrony with a moving image projected onto the device, thereby increasing the integration time for the image, without causing blurring. However, the motion of the signal can be selectively desynchronized from the motion of the radiation image, as required to achieve a desired effect. Further, it should also be understood that while TDI detectors represent an exemplary type of imaging detector, that TDI capability is not required (although TDI does have the advantage of providing a good signal-to-noise ratio). Thus, the concepts disclosed herein encompass collecting image data from the spaced apart imaging regions using imaging detectors that do not implement TDI.

FIG. 8 is a side view (with exaggerated dimensions) of a second embodiment of an exemplary flow imaging system 21 for acquiring images from two different imaging regions that are spaced apart along an axis of motion, which can be used to simultaneously collect a plurality of images from an object in flow from the two different imaging regions using a single detector 44c (having a relatively large field of view), as opposed to using two different detectors. An advantage of using a single detector is cost, as the TDI detectors can represent a substantial percentage of the flow imaging system's cost. In system 21, rather than employing two TDI detectors as in system 20 (see FIGS. 6 and 7), a single detector having a relatively large field of view is employed. Other than the use of a single detector in place of two detectors, system 21 is very similar to system 20. It should be understood that the size of detector 44c in FIG. 8 is exaggerated to emphasize the concept that image data from both imaging region 24a and imaging region 24b is acquired using a single detector. In general, system 21 will not be able to achieve as much magnification as system 20 (because of the requirements for an increased field of view), but that sacrifice is a reasonable tradeoff considering the cost savings (when used with a single six-channel detector, system 21 can provide 12 channels of data at a much lower cost than system 20 can provide when using two six-channel detectors).

FIG. 9 is a schematic diagram of a third embodiment of an exemplary flow imaging system 23 for acquiring images from two different imaging regions that are spaced apart along an axis of motion, which can be used to simultaneously collect a plurality of images from an object in flow from the two different imaging regions using a single detector, where optical components are used to direct light from the first and second imaging regions to the same detector. In this embodiment, the optical components directing light from imaging region 24a to detector 44a are generally the same as those employed in system 20 of FIGS. 6 and 7 (note reflector 25b has been added, as is discussed below). However, the optical components directing light from imaging region 24b have been modified. A reflector 25a and reflector 25b are used to direct light from imaging region 24b to filter stack 36a, imaging lens 40a, and TDI detector 44a (thereby acquiring image data from the second imaging region). Significantly, to prevent image data acquired from imaging region 24a from being confused with image data acquired from imaging region 24b, the relative flow rate of objects being introduced into system 23 must be controlled such that once image data has been acquired from an initial object passing through imaging region 24a, no subsequent object will enter into imaging region 24a until after the initial object travels distance X and image data has been acquired from the initial object passing through imaging region 24b. For a given flow rate, the longer distance X, the longer the timing interval between subsequent objects. As compared to system 21 of FIG. 8, system 23 of FIG. 9 will have a lower throughput, but images can be obtained at a relatively higher magnification. Where a relatively higher throughput is of more importance than a relatively higher magnification, system 21 should be employed. System 21 can also be more advantageously employed where controlling the interval between subsequent objects is difficult; as such control is important to the proper functioning of system 23.

If very good control of the intervals between objects can be achieved, then the throughput of system 23 can be somewhat increased. For example, assume there are two objects, O1 and O2, being imaged. The spacing between the objects can be controlled such that at time T1 object O1 is in imaging region 1 (and image data of object O1 is being acquired from imaging region 1), at time T2 object O1 is moving from imaging region 1 to imaging region 2 and object O2 is in imaging region 1 (and image data of object O2 is being acquired from imaging region 1), at time T3 object O2 is moving from imaging region 1 to imaging region 2 and object O1 is in imaging region 2 (and image data of object O1 is being acquired from imaging region 2), and at time T4 object O1 has moved beyond imaging region 2 and object O2 is in imaging region 2 (and image data of object O2 is being acquired from imaging region 2). This enables throughput to be increased, but requires careful control of the spacing between objects.

Note that the imaging systems shown in FIGS. 6-9, only two separate imaging regions are shown. It should be recognized that if desired, additional spaced apart imaging regions could be employed.

FIG. 10 is a flow chart of an exemplary technique for correcting dynamic cross region spatial offsets from images collected using an imaging system that acquires images from two different imaging regions that are spaced apart along an axis of motion. In a block 60, image data is acquired from two separate imaging regions (spaced apart along an axis of motion), generally as shown in FIGS. 6-9. In some embodiments, image data from each imaging location is TDI image data. In some embodiments, image data from each imaging location is multi-channel image data, including a plurality of different images of the object passing through the imaging region. In some embodiments, the image data represents different spectral images of the object. In some embodiments, a single image can include multiple objects, and spatial offsets can be correct for each object on an object-by-object basis. While the concepts disclosed herein are particularly well suited for use with multi-channel image data, it should be understood that the concepts disclosed herein can also be used where only a single image is collected from each imaging region (as those single images may have a spatial offset error due to an error in the objects estimated velocity).

In a block 62, each object in each image is identified. This is important, because in some cases a plurality of different objects (such as cells) will be passing through each imaging region in close enough proximity that some images may include more than one object. Each such object may be moving at a different speed, which will mean that each object may have a different spatial offset. For example, assume there are three objects close enough together to be in the same image (O1, O2, and O3). The estimated velocity (either based on established fluid flow rates or a measured velocity) of the objects is believed to be X. If the speed of object O1 while moving from the first imaging region to the second imaging region is precisely X, then there likely will be no spatial offset due to a velocity error between the image data acquired from the first imaging region and the image data acquired from the second imaging region (there may be some static spatial offset attributable to the instrument, which can be corrected using the techniques disclosed in U.S. Pat. No. 7,079,708, but there will likely be no spatial alignment error due to a velocity error, unless the velocity error is based on direction rather than speed (rather than moving along a straight line least distance course between the two imaging regions, the object may be moving along a longer path diagonal, and thus will take slightly more time to traverse the distance between the imaging regions). If the speed of object O2 while moving from the first imaging region to the second imaging region is precisely 0.85X (i.e., 15% slower) and the speed of object O3 while moving from the first imaging region to the second imaging region is precisely 1.15X (i.e., 15% faster), then the magnitude of the spatial offset for O2 and O3 will be equal, but the spatial offsets will be in different directions. Clearly, because different objects may have different spatial offsets (because some objects will have different velocity errors), the spatial offset techniques disclosed herein should be applied on an object-by-object basis. In other words, the cross region spatial alignment for object O1 should not be applied to object O2, because objects O1 and O2 may have different velocities, so they may require different spatial offsets to properly align images of objects O1 and O2 acquired from different imaging regions.

Referring once again to FIG. 10, in a block 64, pre-computed spatial offset data will be applied to image data acquired from each imaging region. The step in block 64 is analogous to the spatial offset corrections implemented in U.S. Pat. No. 7,079,708 (indeed, in an exemplary but not limiting embodiment the techniques disclosed in U.S. Pat. No. 7,079,708 are implemented in block 64 for the set of image data acquired from the first imaging region, and also to the set of image data acquired from the second imaging region). Note that because the static spatial corrections being performed in block 64 are a function of the imaging elements (i.e., slightly misaligned optical components or a measurable characteristic of a specific detector) used to acquire the image data (as opposed to inaccurate velocity measurements), different offsets will likely be applied to image data acquired from different imaging regions (because different optical components/detectors are likely to be used). Furthermore, empirical data acquired using the techniques disclosed in U.S. Pat. No. 7,079,708 indicate that spatial errors due to misaligned optical elements or the use of particular detectors are generally static, in that once those offsets have been measured, the measured offsets can be applied to subsequently acquired image data with good results. Thus, in at least one exemplary embodiment, the alignment function implemented in block 64 is based on pre-computed data. However, as discussed in U.S. Pat. No. 7,079,708, such an alignment process can be performed using live data (i.e., contemporaneously acquired data), and the concepts disclosed herein encompass such an embodiment. Block 64 is shown in dashed lines, because under some unique circumstances it may not be required. If calibration studies indicate that no misalignment occurs in image data acquired using a particular combination of optical components and detectors, then no alignment is required (such a scenario is likely to be rare, but is possible). Further, as discussed above, although in at least some exemplary embodiments multiple images (i.e., multi-channel image data) will be acquired from each imaging region, it is possible to use the concepts disclosed herein to align image data acquired from a first imaging region with image data acquired from a second imaging region, where the image data acquired from each imaging region includes only a single image (i.e., single channel data). Even in such single channel data, errors in velocity estimations can induce dynamic cross region spatial offsets between a single image acquired in the first imaging region and a single image acquired in the second imaging region. When only a single image is acquired for each imaging region, there will be no need to spatially align multi-channel image data acquired from a single imaging region, and the step of block 64 would not be needed.

Block 66 also includes a step that is primarily relevant to embodiments in which multi-channel image data is acquired in each imaging region (or at least one of the imaging regions). As discussed above in connection with FIG. 2 (and U.S. Pat. No. 7,079,708), spectral crosstalk between different channels can induce errors in the image data. To be able to properly calculate any dynamic cross regional spatial offset between image data acquired at different imaging regions due to velocity errors, one must have access to images from the first imaging region that are very similar to images from the second region (so the spatial offsets can be measured). Correcting spectral crosstalk from at least one image acquired from the first and second imaging regions will help ensure that similar images from the different data sets (acquired from the different imaging regions) can be compared to compute the spatial offsets induced by the velocity error. While only one of multi-channel images from the first and second data sets (acquired from the different imaging regions) needs to be corrected for such spectral crosstalk to enable the cross region spatial offsets to be calculated (i.e., the spatial offsets induced by a velocity error), such spectral crosstalk correction is in general desirable (as it improves the quality of the image data), and in most embodiments spectral crosstalk correction will be implemented in block 66 for all the image data from each multi-channel. For embodiments where only a single image is acquired from each different imaging region, such spectral crosstalk corrections will not be needed (hence, block 66 is shown as an optional step, necessary only for multi-channel embodiments). It should also be understood that the spectral crosstalk corrections of block 66 need not be implemented in every embodiment where multi-channel image data is acquired.

In a block 68 an image acquired from the first imaging region is compared with an image (of the same object, if multiple objects have been identified) acquired from the second imaging region. The two images are analyzed and X and Y spatial offsets are determined. If multiple objects are present in the image, then different offsets are determined for each object (this is necessary because different objects may be moving at different speeds, or a different velocity error might be associated with different objects). In a block 70, the calculated spatial offsets are used to align each image of each object in the image data acquired from the first imaging region with each image of each object in the image data acquired from the second imaging region. In at least one embodiment, a brightfield image from the image data acquired from the first imaging region is compared with a brightfield image acquired from the second imaging region. In context of the discussion provided below, the images acquired from the first and second imaging regions that are compared to compute the velocity error induced dynamic cross region spatial offsets are referred to as reference images.

FIGS. 11-15 relate to multi-channel image data of biological cells (where some of the cells had been stained with phycoerythrin (a first fluorescent dye) and/or PE-Cy5 (a second fluorescent dye, which is a tandem conjugate that combines phycoerythrin and a cyanine dye)) acquired using an imaging system based on that shown in FIGS. 6-7 (such that a first set of multi-channel image data is acquired from a first imaging region using a first detector, and a second set of multi-channel image data is acquired from a second imaging region using a second detector, the first and second imaging regions being spaced apart along an axis of motion of the biological cells relative to the imaging system). Each set of image data was acquired with a different six-channel TDI camera. This image data (obtained from two different imaging regions) is sometimes referred to below as the empirical image data. The empirical image data was acquired using an imaging system where a 488 nm laser is used to provide illumination to the first imaging region (thereby stimulating emission of certain fluorescent dyes), and a 405 nm laser and a 658 nm laser are used to provide illumination to the second imaging region (thereby stimulating emission of different fluorescent dyes, or different emission profiles for the same dye), noting that the use of such light sources is exemplary and not limiting. In such a system configuration, Ch01 on Camera1 (i.e., the camera acquiring the image data from the first imaging region) is defined as a brightfield channel, and Ch09 on Camera2 (i.e., the camera acquiring the image data from the second imaging region) is defined as a brightfield channel, since those channels will be rarely used based on the laser configuration.

FIG. 11 is a composite image showing brightfield images acquired from both a first imaging region (using a first six channel camera) and a second imaging region (using a second six channel camera), where each brightfield image includes three objects, each of which may be moving at a different speed (thus, each object may exhibit a different velocity error induced spatial offset). The image labeled 1_BF was acquired from a first imaging region, and the image labeled 9_BF was acquired from a second imaging region. Each object is a cell, one or more of which potentially had been stained with PE and/or PE-Cy5. Significantly, the waveband of PE fluorescence does not precisely correspond to the multi-channels of the detector used to acquire the image data, thus there is good chance that the image data exhibits the type of spectral crosstalk discussed above. Correction of such spectral crosstalk will ensure that the images from the first and second imaging regions will be sufficiently similar to enable the velocity error induced spatial offsets to be accurately determined. FIG. 11 corresponds to block 60 of FIG. 10, in that image data has been acquired from different imaging regions, but none of the steps corresponding to the other blocks of FIG. 10 have yet been implemented.

FIG. 12 is a composite image showing the brightfield reference images (i.e., images acquired from the first imaging region and the second imaging region which will be compared to calculate velocity error induced spatial offsets/dynamic cross region spatial offsets), showing the implementation of block 62 of FIG. 10 (the identification of each object in each image). In an exemplary, but not limiting embodiment, individual objects in each image are identified using a segmentation process, such that the segmented images define the region of interest (using a bounding rectangle) for each of the three objects in each image.

The identification of each object in each image is important, because different objects may be moving at different speeds, and thus will require a different X and Y offset for alignment. In an exemplary embodiment, object identification is performed by applying a custom segmentation routine on every image to identify the pixels corresponding to the objects in the image, to generate a mask $M_I$ for Channel I. Each channel mask is then combined to produce a combined mask MC, which is the union of the individual channel masks. Assume there are a total of N channels across all cameras in the imaging system. If mask $M_I^j$ defines the set of pixels corresponding to the $j^{th}$ object in the $I^{th}$ Channel, then the combined mask $MC^j$ is defined as:

$$MC^j = \bigcup_{i=1}^{N} M_i^j \qquad (1)$$

From the combined mask MC, one can identify the set of pixels corresponding to every object using connected component analysis. Essentially, one defines an object as a set of connected pixels in the mask. One can then define the bounding rectangle of every object and extract the corresponding portion of the image from its surroundings, thus isolating each object (FIG. 12). The advantage of using the combined mask to identify the region corresponding to an object is that such a technique is robust to the spatial shifts that can occur in the object between cameras and in the absence of fluorescence intensity in certain channels. It should be understood that the boundary rectangle and mask technique disclosed herein represents an exemplary object identification technique, but that the concepts disclosed herein are not limited to the use of only that technique (i.e., other object identification techniques can be employed).

As noted above, the image in FIGS. 11 and 12 labeled 1_BF was acquired from a first imaging region using a first six-channel camera, while the image labeled 9_BF was acquired from a second imaging region using a second six-channel camera, such that the three objects in each image are the same objects imaged at different times and locations. FIG. 4 and U.S. Pat. No. 7,079,708 both indicate that multi-channel imaging systems often exhibit spatial offsets between different channels due to the optics and detectors used to acquire the image data, and that such offsets are relatively static (i.e., the offsets remain the same even when images of different objects are acquired, because the offsets are a function of the instrument, and not the objects being imaged, or the speed of the objects being imaged). Once the spatial offsets for a specific camera/optical path are determined, those offsets can be applied to subsequently acquired data (so long as no changes have been made to the detector or optical components). FIG. 13A is a Table displaying vertical and horizontal spatial offsets computed for each channel for both the six-channel camera used to acquire the image data from the first imaging region (one such image being labeled 1_BF in FIGS. 11 and 12) and the six-channel camera used to acquire the image data from the second imaging region (one such image being labeled 9_BF in FIGS. 11 and 12). The channels for the first camera have been labeled Ch01-Ch06, and the channels for the second camera have been labeled Ch07-Ch12. For the first camera (used to acquire image data from the first imaging region), Ch05 was defined as the reference channel, with spatial offsets for Ch01, Ch02, Ch03, Ch04 and Ch06 having been computed relative to Ch05. For the second camera (used to acquire image data from the second imaging region), Ch11 was defined as the reference channel, with spatial offsets for Ch07, Ch08, Ch09, Ch10 and Ch12 having been computed relative to Ch11. Note that U.S. Pat. No. 7,079,708 discloses a technique that can be used to determine the instrument based spatial offsets for a multi-channel imaging system (noting that such techniques are exemplary and not limiting).

The offsets identified in FIG. 13A enable the step shown in block 64 of FIG. 10 to be implemented for a specific imaging system including two specific six-channel cameras. Note that such offsets are a function of the specific hardware used to acquire image data (i.e., the specific optical components and the specific detector used to collect the image data from each imaging region), and such offset data must be uniquely determined for each different imaging system/detector. FIG. 4 graphically illustrates image data in a four-channel detector being spatially misaligned due to an optical path/detector misalignment unique to a specific imaging system, and the offset data of FIG. 13A (and the step shown in block 64 of FIG. 10) is used to spatially align images in different detector channels for each imaging region for the specific imaging system used to acquire the image data of FIGS. 11 and 12.

FIG. 13B is a Table displaying a 12×12 crosstalk matrix computed for all 12 channels of the 2-camera (6-channels each) imaging system used to acquire the empirical image data. This matrix enables the step shown in block 66 (spectral crosstalk correction) to be implemented. U.S. Pat. No. 7,079,708 discloses techniques for correcting for spectral crosstalk in a multi-channel imaging system. Spectral offsets for the camera used to acquire empirical image data from the first imaging region are provided in box 51, while spectral offsets for the camera used to acquire empirical image from the second imaging region are provided in box 53. Essentially, the 12×12 matrix specifies how much spectral crosstalk leaks into each channel. The matrix has a "1" in the channel where a particular dye is brightest. The values for all other channels are less than one, and specify the spillover that must be corrected via spectral compensation. So, the 12×12 matrix actually contains the coefficients to 12 simultaneous equations that must be solved in order to pull out the spillover. Significantly, the spectral compensation cannot be performed until the imagery in each channel is spatially aligned (i.e., the step of block 64 must be implemented before the step of block 66).

Note that the spectral crosstalk correction is important to perform before calculating the dynamic spatial offsets between a reference image acquired from the first imaging region with a reference image acquired from the second imaging region (to calculate the cross region spatial offsets between the image data acquired from the first imaging region and the image data acquired from the second imaging region, where the cross region spatial offset is a function of an error in an estimated speed of objects moving between the first and second imaging regions), because the reference images need to be similar to obtain accurate cross region spatial offsets. Spectral crosstalk in the reference images can make the images look dissimilar. The spectral crosstalk in the reference images (from the first and second imaging regions) is solved by first using the pre-computed spatial offsets (the offsets shown in FIG. 13A, which are a function of the instrument used to acquire the multi-channel data, and not an error in the estimated speed of the objects moving between the imaging regions) for the different channels in each multi-channel detector, to align the images acquired by each detector relative to each other. Then, the crosstalk matrix of FIG. 13B is used to apply spectral corrections. The data in the top left quadrant of the crosstalk matrix (box 51) is applied to each object in the image data from acquired by the first camera (the camera obtaining image data from the first imaging region) and the data in the bottom right quadrant (box 53) is applied to each object in the image data acquired by the second camera (the camera obtaining image data from the second imaging region).

FIG. 14 is a composite image showing empirical image data acquired from both the first imaging region (using the first six-channel camera) and the second imaging region (using the second six-channel camera), after applying the steps of blocks 62 and 64 of FIG. 10 (i.e., individual objects in images have been identified and the instrument specific spatial offsets for the plurality of different channels have been applied to align the images acquired from the first imaging region with each other, and to align the images acquired from the second imaging region with each other, but the spectral crosstalk between channels has not been reduced (the spectral crosstalk reduction corresponds to block 66 of FIG. 10)). Referring to FIG. 14, each row represents an image of the same object taken from a different data channel. The images labeled 1_BF (Ch01 of Camera1) are brightfield images acquired from the first imaging region, the images labeled 9_BF (Ch09 of Camera2) are brightfield images acquired from the second imaging region, and the images labeled 3_PE (Ch03 of Camera1) are spectral images corresponding to the emission peak for PE (only cells having been stained with PE will be present in such images) acquired from the first imaging region. The brightfield images from each camera are used as reference images; i.e., the relative spatial position of an object in a 1_BF image (Ch01 of Camera1) is compared to the relative spatial position of the corresponding object in a 9_BF image (Ch09 of Camera2) to determine how much dynamic cross region spatial offset is due to a velocity error (this is the process of block 68 of FIG. 10). Note the 1_BF images (Ch01 of Camera1) and 9_BF images (Ch09 of Camera2) in FIG. 14 have not been aligned based on the offsets that are determined in block 68 of FIG. 10. Note that the upper 1_BF image (Ch01 of Camera1) and the upper 9_BF image (Ch09 of Camera2) are already fairly well aligned, indicating that there is very little error in the estimated velocity of that object moving between the first and second imaging regions. However, the middle 1_BF image (Ch01 of Camera1) and the middle 9_BF image (Ch09 of Camera2) are not well aligned, particularly in the horizontal (X) axis, and the bottom 1_BF image and the bottom 9_BF image (Ch09 of Camera2) are also not well aligned, particularly in both the horizontal (X) axis and the vertical (Y) axis. The spatial offsets in the middle and lower 9_BF images (Ch09 of Camera2) are due in part to significant spectral cross-camera crosstalk from PE in Ch03, with the effect being proportional to the intensity of the PE signal. The images from FIG. 14 emphasize a very bright PE image in Ch03 that can cause the reference image in Ch09 to look very different from the corresponding reference image in Ch01 (noting that the reference images are of the same object acquired from the different cameras at the different imaging regions) due to spectral crosstalk across cameras (i.e., across the different imaging regions).

FIG. 14 thus graphically illustrates the problem with having spectral crosstalk in the reference images that are to be used to determine the cross region spatial offsets (i.e., unless the reference image from the first imaging region and the reference image from the second imaging region (both images of the same object) are very similar in appearance, the cross regions spatial offset cannot be accurately determined). Spectral crosstalk can make such reference images appear very different. No matter how well the lasers used to illuminate the different imaging regions (to stimulate fluorescent dyes that some of the cells may have been tagged with) are spatially separated, in some cases cross region spectral crosstalk will be a problem when dealing with dyes, such as PE, that are stimulated by multiple wavelengths. In a specific example, cells are tagged with PE (which is strongly stimulated using a 488 nm laser, but other wavelengths of light, such as light emitted by a 405 nm laser, will also induce some fluorescence in PE). The first imaging region is illuminated with a 488 nm laser, and Camera1 of the imaging system is configured to acquire images corresponding to PE fluorescent emissions in Ch03. Camera2 of the imaging system is configured to acquire a brightfield image in Ch09. If the second imaging region is illuminated by a 405 nm laser to stimulate a strong emission from a different dye, any PE present will fluoresce to some extent (even though a larger emission will be stimulated by the 488 nm light in the first imaging region), and the PE fluorescent stimulated by the 405 nm light in the second imaging region will "bleed" into the brightfield image in Ch09 of Camera2. The PE spectral crosstalk present in Ch09 of Camera2 will cause the brightfield reference image in Ch09 of Camera2 to look different than the brightfield reference image acquired by Camera1 from the first imaging region. Relatively larger amounts of this type of cross region spectral crosstalk will make the reference images look different, and the more different the reference images look, the more difficult it is to determine the cross region spatial offsets due to an error in an estimated velocity of the object moving between the imaging regions (i.e., relatively more spectral crosstalk will make the implementation of block 68 of FIG. 10 less accurate). For example, assume there is 5% crosstalk into a reference BF (brightfield) channel from a fluorescent channel, where the maximum pixel intensity is of the order of 4000. This will result in 0.05*4000=200 counts of pixel intensity added to the reference BF channel. Further assume that the BF image has a mean background value of 800 with a range of 400. This means that a crosstalk coefficient as low as 5% can add 100*200/800=25% crosstalk into the BF channel. This can make the BF image with the crosstalk look very different from its counterpart BF image on the other camera which may not have the crosstalk. In the example shown in FIG. 14, the spectral crosstalk from Ch03 into Ch09 is 32.5%, resulting in a very significant cross region spectral crosstalk problem. To solve this crosstalk problem, one needs to correct for the spectral crosstalk between cameras in addition to the spectral crosstalk within each camera. However, this poses a dilemma that needs to be resolved. In order to correct for the spectral cross-camera crosstalk, one must spatially align the image data between the two cameras first, but that cannot be accomplished if the cross region spectral crosstalk prevents the cross region spatial offsets from being determined.

The dilemma noted above is solved using a novel approach. Since the cross-camera crosstalk cannot be removed from the reference images, instead one can add the same amount of crosstalk to the within camera reference image, thus making the two images similar. In the above example, one cannot correct the 32.5% crosstalk from Ch03 into the reference image Ch09. Instead, one adds the 32.5% crosstalk from Ch03 into the reference image from Ch01. This makes the images in Ch01 and Ch09 look similar (both are BF+the same crosstalk) as required for accurate alignment offset computation. The data in the Table of FIG. 13B enables these spectral crosstalk corrections to be made.

FIG. 15 is a flowchart illustrating an exemplary sequence for aligning different channels of the empirical image data. It should be understood that FIG. 15 is related to the more general method of FIG. 10, in that the method of FIG. 15 is only implemented where multi-channel image data is acquired from each imaging region (whereas the method of FIG. 10 can be implemented for image data where only a single image is acquired from each different imaging region, and the steps of blocks 64 and 66 of FIG. 10, specific to multi-channel image data, are not needed). Further, the order of the steps of FIG. 15 have been modified as compared to the method of FIG. 10, illustrating how the same overall function of correcting dynamic spatial offsets between the image data acquired from spaced apart imaging can be performed by modifying the exemplary steps of FIG. 10.

Referring to FIG. 15, the image data acquired from each imaging region is processed to identify each object, to remove background from object images to highlight the object features (so that only the actual object is highlighted), to smooth the resulting object image using an averaging filter to reduce noise spikes (as such noise spikes might adversely affect the alignment computation), to obtain (via cross-correlation) a matrix of correlations for all valid pixel shift positions, such that the location of the maximum correlation is determined, and finally to obtain a sub-pixel shift location (i.e., X and Y spatial offsets) using a polynomial fit around the coarse maximum correlation.

The cross correlation element refers to a normalized cross correlation between the two reference image objects (such as are shown in FIG. 14 as 1_BF and 9_BF images, noting that the use of brightfield images as reference images is exemplary, rather than limiting), which is performed to generate a correlation matrix containing the normalized correlation values for valid pixel shifts in both the X and Y directions. The maximum correlation is found, and the corresponding X and Y locations determined. Then by using N points around the maximum, the sub-pixel shift in X and Y is determined using a polynomial fit. In an exemplary implementation, for simplicity and computational ease, the fit is restricted to use only the immediate neighborhood correlation values (N=1).

The cross correlation $R_{xy}(r,c)$ between an image x and an image y at the pixel in row r and column c is computed by the equation:

$$R_{xy}(r, c) = \sum_{j=0}^{tplRows-1} \sum_{i=0}^{tplCols-1} x(j, i).y\left(r + j - \frac{tplRows}{2}, c + i - \frac{tplCols}{2}\right) \quad (2)$$

The normalized cross correlation function between the image x and image y is then computed as follows:

$$\rho_{xy}(r, c) = \frac{R_{xy}(r, c)}{\sqrt{R_{yy}(r, c)R_{xx}\left(\frac{tplRows}{2}, \frac{tplsCols}{2}\right)}} \quad (3)$$

where $R_{xx}$ and $R_{yy}$ denote the auto-correlation of image x and image y respectively and are defined as:

$$R_{xx}\left(\frac{tplRows}{2}, \frac{tplCols}{2}\right) = \sum_{j=0}^{tplRows-1} \sum_{i=0}^{tplCols-1} x_{j,i} x_{j,i} \quad (4)$$

and $$R_{yy}(r, c) = \sum_{j=r-\frac{tplRows-1}{2}}^{r+\frac{tplRows-1}{2}} \sum_{i=c-\frac{tplCols-1}{2}}^{c+\frac{tplCols-1}{2}} y_{j,i} y_{j,i} \quad (5)$$

FIGS. 16A-16C graphically illustrate a normalized cross-correlation surface for the object images in FIG. 15 with a clear peak. The location of the peak is used to obtain the gross alignment offset. The offset is then refined to sub-pixel precision using a polynomial fit around the peak using the immediate neighborhood of 1 point on each side. FIG. 16A graphically illustrates a normalized cross-correlation surface plot, where the X and Y axis on the plot are pixel shifts, and the Z axis is the corresponding normalized cross-correlation value. FIG. 16B graphically illustrates the normalized cross-correlation surface plot of FIG. 16A as seen from above. FIG. 16C graphically illustrates a zoomed in view of the normalized cross-correlation surface plot of FIG. 16A, to show the highest value location.

Once the X and Y offsets between the image data acquired from the two spaced apart imaging regions have been computed, they are applied to align the images acquired from the different imaging regions. FIG. 17 generally corresponds to FIG. 14, after the method shown in FIG. 15 (and the multi-channel image embodiment of the method of FIG. 10) has been implemented to spatially align the images acquired at the different imaging regions.

In addition to the modification of the method steps of FIG. 10 indicated in FIG. 15, it should be recognized that the exemplary method of FIG. 10 can be modified in other ways to achieve the same type of dynamic spatial offset corrections, where the dynamic spatial offset between images acquired at a first imaging region and a second imaging region (where the imaging regions are spaced apart along an axis of motion) are due to an error in an estimated velocity of the object as it moves between the two imaging regions. FIG. 18 represents one such modification, where each set of image data acquired from each of the two spaced apart imaging regions includes multi-channel image data (i.e., such as the multi-channel empirical data discussed above, acquired using an imaging system based on FIG. 6, with two spaced apart six-channel cameras; Camera1 and Camera2). In block 60 (performing the same function as block 60 in FIG. 10) the image data is acquired from Camera1 and Camera2. The image data includes six channels of data from Camera1 (Ch01-Ch06) and six channels of data from Camera2 (Ch07-Ch12). In block 62 (once again performing the same function as block 62 in FIG. 10), each object in each image is identified (because different objects may be moving at different speeds, the method is implemented on an object-by-object basis). In a block 63 (representing a departure from the sequence of steps in FIG. 10), a Reference Image 1 from Camera1 and a Reference Image 2 from Camera2 are selected. In context of the empirical data discussed above, the reference images are brightfield images. Reference Image 1 from Camera1 is from Ch05, and Reference Image 2 from Camera2 is from Ch11.

In a block 64*a* (generally corresponding to the functions of blocks 64 and 66 in FIG. 10, applied only to the reference images), any static spatial offsets and spectral crosstalk corrections needed to make the reference images more similar are implemented. The static spatial offsets are the offsets between different data channels arising from specific optical components and detectors (see FIG. 13A). Note that if Reference Image 1 is selected from the reference channel that other channels in Camera1 are aligned to when performing the static spatial offset correction (discussed above with respect to FIG. 13A), then no static spatial offsets need to be applied to Reference Image 1. Referring to FIG. 13A, note that there is no spatial offset for Ch05, because the static offset data will be used to align image data from the other channels in Camera1 (i.e., channels Ch01, Ch02, Ch03, Ch04 and Ch06) to the image data in Ch05. Similarly, FIG. 13A provides no static spatial offset for Ch11, because the static offset data will be used to align image data from the other channels in Camera2 (i.e., channels Ch07, Ch08, Ch09, Ch10 and Ch12) to the image data in Ch11. Thus, for the special case where the reference images are selected from the data channel also used as the reference channel for the static spatial offsets, no static spatial offset is required for the reference images. The cross correlation function relating to the Table in FIG. 13B is then used to make spectral corrections to the reference images. In a block 68*a* (performing the same function as block 68 in FIG. 10), the dynamic spatial offsets between Reference Image 1 from Camera1 and Reference Image 2 from Camera2 are computed. In a block 70*a*, all images from Camera2 are aligned to Reference Image 1 using the computed dynamic spatial offset determined in block 68*a*. Then, in a block 72, the static spatial offsets for Ch01, Ch02, Ch03, Ch04, and Ch06 are used to align images from those channels to Reference Image 1 (which is from Ch05). Finally, in a block 74, the static spatial offsets for Ch07, Ch08, Ch09, Ch10, and Ch12 are used to align images from those channels to Reference Image 2 (which is from Ch11). It should be recognized that ultimately the methods of FIGS. 10 and 18 achieve the same result, of correcting for dynamic spatial offsets between images obtained from two spaced apart imaging regions, where the dynamic spatial offsets are related to an error in an estimated velocity of an object being imaged as it moves between the two imaging regions. The primary difference between the methods of FIGS. 10 and 18 is when the static spatial offsets are applied.

With respect to the method of FIG. 18 and the empirical imaging system based on FIG. 6 (including Camera1 and Camera2, each camera having six data channels) used to collect the empirical data discussed, Camera1 and Camera2 each have a total of 6 channels, with Ch05 being the reference channel for the within camera spatial offset computation for Camera1, and Ch11 the reference channel for the within camera spatial offset computation for Camera2. Let A denote the reference channel image on Camera1 and B the reference channel image on Camera2. In an exemplary implementation based on FIG. 18 (where static spatial offset correction in block 64*a* is required), A is Ch01 and B is Ch09. Then, the spatial offsets in X and Y for each channel on the two cameras with respect to the Camera1 spatial offset reference channel (Ch05 in the empirical imaging system) is computed as follows:

$$\overline{X}_{offset}(i) = X_{offset}(i); 1 \le i \le 6$$

$$\overline{X}_{offset}(i) = X_{offset}(i) - X_{offset}(B) + X_{offset}(A); 6 \le i \le 12$$

$$\overline{Y}_{offset}(i) = Y_{offset}(i); 1 \le i \le 6$$

$$\overline{Y}_{offset}(i) = Y_{offset}(i) - Y_{offset}(B) + Y_{offset}(A); 6 \le i \le 12$$

Referring once again to FIG. 10, when applying the method to multi-channel image data, in general the static offsets (block 64; which corrects for spatial offsets among different images collected from the same imaging region due to parameters unique to a specific combination of optical components and detector) are applied before the dynamic offsets (block 70; which corrects for spatial offsets for images of the same object collected at different times at different imaging regions due to an error in an estimated velocity of the object moving between the two imaging regions) are applied, because the static offsets may be needed to determine spectral crosstalk corrections (which if not corrected can reduce the accuracy of the determination of the dynamic spatial offsets). In addition to the embodiment of FIG. 18, in at least one additional implementation, the static offsets can be implemented after the dynamic offsets. In such an implementation, no spectral crosstalk corrections are required, and the reference image from the image data acquired from the first imaging region and the reference image from the image data acquired from the second imaging region (which are compared to calculate the dynamic spatial offsets) require no static offsets, because each reference image is from the specific channel that the static offset data is derived from. Note that in FIG. 13A, no static offsets are applied to either Ch05 (of the multi-channel camera used to acquire image data from the first region) or Ch11 (of the multi-channel camera used to acquire image data from the second region), because the image data from other channels are adjusted to align with the image data in Ch05 (for the first camera) and Ch11 (for the second camera). Thus, the dynamic spatial offsets can be determined by comparing the image of an object in Ch05 with the image of the same object in Ch11, before the static offsets are applied to Ch01, Ch02, Ch03, Ch04, and Ch06 (for the multi-channel camera used to acquire image data from the first region) or to Ch07, Ch08, Ch09, Ch10, and Ch12 (for the multi-channel camera used to acquire image data from the second region).

In implementations where the dynamic spatial offsets are calculated by selecting one reference image from among a plurality of different images acquired at two different imaging regions (the selected image from the image data set acquired from the first imaging region and the selected image from the image data set acquired from the second imaging region being referred to as a reference image), using a brightfield image as a reference image is particularly useful. While two fluorescent images (such as PE images) could be used to calculate the dynamic spatial offset (the spatial offset between image data acquired from the first imaging region and the image data acquired from the second imaging region), the use of a brightfield image has two main advantages: (1) all cells for which image data will be acquired will exhibit a brightfield image, which is not the case with fluorescence (i.e., some cells may not be labeled with a particular fluorescent dye, thus not all cells will exhibit an image in a spectral channel corresponding to such a fluorescent dye); and (2) brightfield imagery can generally be collected from any channel in a multi-channel camera, and brightfield images are not restricted to a particular spectral bandwidth. This provides flexibility in designing specific experimental studies, because the user can designate any channel corresponding to the spectral waveband of a fluorescent dye not being used in the experiment as a brightfield channel (i.e., in some studies the user can use Ch03 to acquire a PE image, but in studies where PE is not used, Ch03 can be used to acquire a brightfield image).

Exemplary Computing Environment

As discussed above, a key aspect of the concepts disclosed herein involves post image acquisition processing to enhance the image data, by aligning image data acquired from two different imaging regions spaced apart along an axis of motion between the imaging system and the object being imaged. Such image processing corrects for dynamic spatial alignment errors introduced by an error in an estimated velocity of the object being imaged as it moves between the two imaging regions (and in order to achieve such dynamic spatial alignment, in some embodiments static spatial alignments unique to the optics/detector of a specific imaging system also need to be corrected). FIG. 19 schematically illustrates an exemplary computing system 250 suitable for use in implementing the method of FIG. 10 (or the method of FIGS. 15 and/or 18, as desired). Exemplary computing system 250 includes a processing unit 254 that is functionally coupled to an input device 252 and to an output device 262, e.g., a display (which can be used to output a result to a user, although such a result can also be stored). Processing unit 254 comprises, for example, a central processing unit (CPU) 258 that executes machine instructions for performing the dynamic spatial alignment technique disclosed herein (which in at least some embodiments includes spectral crosstalk corrections and static spatial alignments). The machine instructions implement functions generally consistent with those described above with respect to the methods of FIGS. 10, 15, and 18. CPUs suitable for this purpose are readily available, for example, from Intel Corporation, AMD Corporation, Motorola Corporation, and other sources, as will be well known to those of ordinary skill in this art.

Also included in processing unit 254 are a random access memory (RAM) 256 and non-volatile memory 260, which can include read only memory (ROM) and may include some form of memory storage, such as a hard drive, an optical disk (and drive), etc. These memory devices are bi-directionally coupled to CPU 258. Such storage devices are well known in the art. Machine instructions and data are temporarily loaded into RAM 256 from non-volatile memory 260. Also stored in the memory are an operating system software and ancillary software. While not separately shown, it will be understood that a generally conventional power supply will be included to provide electrical power at a voltage and current level appropriate to energize the components of computing system 250.

Input device 252 can be any device or mechanism that facilitates user input into the operating environment, including, but not limited to, one or more of a mouse or other pointing device, a keyboard, a microphone, a modem, or other input device. In general, the input device will be used to initially configure computing system 250, to achieve the desired processing (e.g., to process image data to produce images as discussed above). Configuration of computing system 250 to achieve the desired processing includes the steps of loading appropriate processing software into non-volatile memory 260, and launching the processing application (e.g., loading the processing software into RAM 256 for execution by the CPU) so that the processing application is ready for use. Output device 262 generally includes any device that produces output information, but will most typically comprise a monitor or computer display designed for human visual perception of output. Use of a conventional computer keyboard for input device 252 and a computer display for output device 262 should be considered as exemplary, rather than as limiting on the scope of this system. Data link 264 is configured to enable image data collected from a flow imaging system to be introduced into computing system 250 for subsequent image processing as discussed above. Those of ordinary skill in the art will readily recognize that many types of data links can be implemented, including, but not limited to, universal serial bus (USB) ports, parallel ports, serial ports, inputs configured to couple with portable memory storage devices, FireWire (conforming to I.E.E.E. 1394 specification) ports, infrared data ports, wireless data ports such as Bluetooth™, network connections such as Ethernet ports, and Internet connections.

FIG. 20 is a schematic diagram of an exemplary flow imaging system 350 for acquiring images from two different imaging regions that are spaced apart along an axis of motion, which can be used to simultaneously collect a plurality of images from an object in flow from the two different spaced apart imaging regions, where a common objective 358 is used to acquire light from a field of view that encompasses both imaging regions.

Objects such as cells are introduced into a flow cell 352. A first light source 354 illuminates a first imaging region 351, and a second light source 356 illuminates a second imaging region 353 (note the imaging regions are indeed spaced apart, although the scale of this Figure does not exaggerate the spacing to the extent of FIGS. 6 or 9). Light from a field of view encompassing both imaging regions is acquired by objective 358, and directed along an optical path including lens 360 to a slit 362. Light from the first imaging region is diverted along an optical path including a lens 364, a dichroic filter element 366 (generally as discussed above with respect to FIG. 5B), and lens 368, which generates spectrally dispersed images onto a first camera 370. Light from the second imaging region is directed along an optical path including a lens 372, a dichroic filter element 374 (generally as discussed above with respect to FIG. 5B), and lens 376, which generates spectrally dispersed images onto a second camera 378.

Although the concepts disclosed herein have been described in connection with the preferred form of practicing them and modifications thereto, those of ordinary skill in the The invention in which an exclusive right is claimed is defined by the following:

1. A method for correcting spatial alignment errors in an imaging system that acquires images of an object from at least two spatially distinct imaging regions at different times, while there is relative motion between the object and each imaging region, comprising the steps of:
   (a) acquiring at least one image of the object from a first imaging region at a first point in time;
   (b) acquiring at least one image of the object from a second imaging region at a second point in time, the first imaging region and the second imaging region being spatially separated, the first point in time and the second point in time being temporally separated, where acquisition of each image of the object from the second imaging region is based on an estimated speed of the relative motion between the object and each imaging region;
   (c) determining a cross region spatial misalignment between image data acquired from the first imaging region and image data acquired from the second imaging region by analyzing image data acquired from the first and second imaging regions, where the cross region spatial misalignment is proportional to an error in the estimated speed; and
   (d) correcting the cross region spatial misalignment to align the image data acquired from the first region with the image data acquired from the second region.

2. The method of claim 1, wherein a plurality of images of the object are simultaneously acquired from the first imaging region to obtain a first set of images, a plurality of images of the object are simultaneously acquired from the second imaging region to obtain a second set of images, and before implementing the steps of determining and correcting the cross region spatial misalignment, implementing the steps of:
   (a) using first predetermined offset data corresponding to the first imaging region to spatially align each image in the first set of images; and
   (b) using second predetermined offset data corresponding to the second imaging region to spatially align each image in the second set of images.

3. The method of claim 2, wherein after the steps of using the first predetermined offset data to align the plurality of images in the first set of images and using the second predetermined offset data to align the plurality of images in the second set of images, and before implementing the steps of determining and correcting the cross region spatial alignment, performing the steps of:
   (a) correcting spectral crosstalk in the first set of images; and
   (b) correcting spectral crosstalk in the second set of images.

4. The method of claim 3, wherein the step of correcting spectral crosstalk in the first set of images comprises the step of correcting for spectral crosstalk in a first brightfield reference channel image from the first set of images, and the step of correcting spectral crosstalk in the second set of images comprises the step of correcting for spectral crosstalk in a second brightfield reference channel image from the second set of images.

5. The method of claim 4, wherein the step of determining the cross region spatial misalignment comprises the step of determining a spatial misalignment between the first brightfield reference channel image and the second brightfield reference channel image.

6. The method of claim 1, wherein the step of acquiring the at least one image of the object from the first imaging region and the step of acquiring the at least one image of the object from the second imaging region are implemented using a common imaging device.

7. The method of claim 1, wherein the step of acquiring the at least one image of the object from the first imaging region and the step of acquiring the at least one image of the object from the second imaging region are implemented using a first imaging device for the first imaging region and a second imaging device for the second region.

8. The method of claim 1, wherein image data acquired from the first imaging region and the second imaging region includes images containing more than just one object, such that the steps of determining and correcting the cross region spatial misalignment is applied to each individual object in the images acquired from the first and second imaging regions, as objects moving at different speeds will exhibit different cross region spatial misalignments.

9. An imaging system for acquiring images of an object from at least two spatially distinct imaging regions at different times, while there is relative motion between the object and each imaging region, the imaging system comprising:
   (a) a first imaging component for acquiring at least one image of an object from a first imaging region at a first point in time;
   (b) a second imaging component for acquiring at least one image of the object from a second imaging region at a second point in time, the first imaging region and the second imaging region being spatially separated, acquisition of each image of the object from the second imaging region being based on an estimated speed of the relative motion between the object and each imaging region; and
   (c) a processor logically coupled to the first and second imaging components, the processor configured to implement a spatial alignment technique using the functions of:
      (i) determining a cross region spatial misalignment between image data acquired from the first imaging region and image data acquired from the second imaging region by analyzing image data acquired from the first and second imaging regions, where the cross region spatial misalignment is proportional to an error in the estimated speed; and
      (ii) correcting the cross region spatial misalignment to align the image data acquired from the first region with the image data acquired from the second region.

10. The imaging system of claim 9, wherein the first and second imaging components are configured to simultaneously acquire a plurality of images of the object, and the processor is configured to implement the following functions before determining and correcting the cross region spatial misalignment:
    (a) using first predetermined offset data for the first imaging component to spatially align each image acquired by the first imaging component; and
    (b) using second predetermined offset data for the second imaging component to spatially align each image acquired by the second imaging component.

11. The imaging system of claim 10, wherein the processor is configured to implement the following functions before determining and correcting the cross region spatial misalignment:

(a) correcting for spectral crosstalk in at least a first reference image acquired from the first imaging component; and (b) correcting for spectral crosstalk in at least a second reference image acquired from the second imaging component.

12. The imaging system of claim 9, wherein the first and second imaging components comprise a single multi-channel imaging detector configured to acquire image data from both the first imaging region and the second imaging region.

13. The imaging system of claim 9, wherein image data acquired from the first imaging region and the second imaging region includes images containing more than just one object, and the processor implements the steps of determining and correcting the cross region spatial misalignment to each individual object in the images acquired from the first and second imaging regions, as objects moving at different speeds will exhibit different cross region spatial misalignments.

14. A method for correcting spatial alignment errors in a multi-channel imaging system that acquires multi-channel images of an object from at least two spatially distinct imaging regions at different times, while there is relative motion between the object and each imaging region, comprising the steps of:

(a) acquiring multi-channel images of an object from a first imaging region, thereby acquiring a first set of images;

(b) acquiring multi-channel images of an object from a second imaging region after acquisition of the first set of images, thereby acquiring a second set of images, the first imaging region and the second imaging region being spatially separated, where acquisition of the multi-channel images of the object from the second imaging region is based on an estimated speed of the relative motion between the object and each imaging region;

(c) using first predetermined offset data corresponding to hardware used to acquire image data from the first imaging region to spatially align each image in the first set of images;

(d) using second predetermined offset data corresponding to hardware used to acquire image data from the second imaging region to spatially align each image in the second set of images;

(e) determining a cross region spatial misalignment between the first set of images and the second set of images by analyzing image data from the first and second set of images, where the cross region spatial misalignment is proportional to an error in the estimated speed; and (f) correcting the cross region spatial misalignment to spatially align the first set of images with the second set of images.

15. The method of claim 14, wherein after the steps of using the first predetermined offset data to align each image in the first set of images and using the second predetermined offset data to align each image in the second set of images, and before implementing the steps of determining and correcting the cross region spatial alignment, performing the steps of:

(a) correcting spectral crosstalk in the first set of images; and (b) correcting spectral crosstalk in the second set of images.

16. The method of claim 14, wherein the step of correcting spectral crosstalk in the first set of images comprises the step of correcting for spectral crosstalk in a first brightfield reference channel image from the first set of images, and the step of correcting spectral crosstalk in the second set of images comprises the step of correcting for spectral crosstalk in a second brightfield reference channel image from the second set of images.

17. The method of claim 14, wherein the step of determining the cross region spatial misalignment comprises the step of determining a spatial misalignment between a first brightfield reference channel image in the first set of images and a second brightfield reference channel image in the second set of images.

18. The method of claim 14, wherein the steps of acquiring the first set of images from the first imaging region and the step of acquiring the second set of images from the second imaging region are implemented using a first imaging device for the first imaging region and a second imaging device for the second region.

19. The method of claim 14, wherein the steps of acquiring the first set of images from the first imaging region and the step of acquiring the second set of images from the second imaging region are implemented using common hardware, such that the first and second predetermined offset data are the same.

20. The method of claim 14, wherein image data acquired from the first imaging region and the second imaging region includes images containing more than just one object per image, such that the steps of using the first predetermined offset data corresponding to the first imaging region, using the second predetermined offset data corresponding to the second imaging region, determining the cross region spatial misalignment between the first set of images and the second set of images, and correcting the cross region spatial misalignment is applied to each individual object in each image acquired from the first and second imaging regions, as objects moving at different speeds will exhibit different cross region spatial misalignments.

21. The method of claim 14, wherein acquisition of the first and second set of images involves time delay integration.

22. An imaging system for acquiring multi-channel images of an object from at least two spatially distinct imaging regions at different times, while there is relative motion between the object and each imaging region, the imaging system comprising:

(a) a first imaging component for acquiring multi-channel images of an object from a first imaging region, thereby acquiring a first set of images;

(b) a second imaging component for acquiring multi-channel images of the object from a second imaging region, thereby acquiring a second set of images, the second set of images being acquired after the first set of images, the first imaging region and the second imaging region being spatially separated, acquisition of each image of the object from the second imaging region being based on an estimated speed of the relative motion between the object and each imaging region; and (c) a processor logically coupled to the first and second imaging components, the processor configured to implement a spatial alignment technique using the functions of:

(i) using first predetermined offset data corresponding to the first imaging component to spatially align each image in the first set of images;

(ii) using second predetermined offset data corresponding to the second imaging component to spatially align each image in the second set of images;

(iii) determining a cross region spatial misalignment between image data acquired from the first imaging region and image data acquired from the second imaging region by analyzing image data acquired from the first and second imaging regions, where the cross region spatial misalignment is proportional to an error in the estimated speed; and (iv) correcting the cross region spatial misalignment to align the image data acquired from the first region with the image data acquired from the second region.

23. The imaging system of claim 22, wherein the processor is configured to implement the following functions before determining and correcting the cross region spatial misalignment:

(a) correcting for spectral crosstalk in at least a first reference image acquired from the first imaging component; and (b) correcting for spectral crosstalk in at least a second reference image acquired from the second imaging component.

24. The imaging system of claim 22, wherein the first and second imaging components comprise a single multi-channel imaging detector configured to acquire image data from both the first imaging region and the second imaging region.

25. The imaging system of claim 22, wherein image data acquired from the first imaging region and the second imaging region includes images containing more than just one object, and the processor implements the steps of using the first predetermined offset data corresponding to the first imaging region, using the second predetermined offset data corresponding to the second imaging region, determining the cross region spatial misalignment between the first set of images and the second set of images, and correcting the cross region spatial misalignment on an object-by-object basis, as objects moving at different speeds will exhibit different cross region spatial misalignments.

26. A non-transitory memory medium having machine instructions stored thereon for implementing an automated spatial alignment technique in an imaging system for acquiring multi-channel images of an object from at least two spatially distinct imaging regions at different times, while there is relative motion between the object and each imaging region, the machine instructions, when implemented by a processor, carrying out the functions of:

(a) using first predetermined offset data corresponding to a first imaging component in the imaging system to spatially align each image in a first set of images acquired from a first imaging region;

(b) using second predetermined offset data corresponding to a second imaging component in the imaging system to spatially align each image in a second set of images acquired from a second imaging region;

(c) determining a cross region spatial misalignment between image data acquired from the first imaging region and image data acquired from the second imaging region by analyzing image data acquired from the first and second imaging regions, where the cross region spatial misalignment is proportional to an error in the estimated speed; and (d) correcting the cross region spatial misalignment to align the image data acquired from the first region with the image data acquired from the second region.

27. The non-transitory memory medium of claim 26, wherein the machine instructions, when implemented by a processor, enable the following functions to be performed before determining and correcting the cross region spatial misalignment:

(a) correcting for spectral crosstalk in at least a first reference image acquired from the first imaging component; and (b) correcting for spectral crosstalk in at least a second reference image acquired from the second imaging component.

* * * * *